(12) United States Patent
Berkley et al.

(10) Patent No.: US 7,880,717 B2
(45) Date of Patent: Feb. 1, 2011

(54) METHOD, APPARATUS, AND ARTICLE FOR FORCE FEEDBACK BASED ON TENSION CONTROL AND TRACKING THROUGH CABLES

(75) Inventors: Jeffrey J. Berkley, Seattle, WA (US); Seahak Kim, Seoul (KR); Sungkwan Hong, Kanagawa-ken (JP)

(73) Assignee: Mimic Technologies, Inc., Seattle, WA (US)

( * ) Notice: Subject to any disclaimer, the term of this patent is extended or adjusted under 35 U.S.C. 154(b) by 607 days.

(21) Appl. No.: 10/811,310

(22) Filed: Mar. 26, 2004

(65) Prior Publication Data
US 2005/0024331 A1    Feb. 3, 2005

Related U.S. Application Data

(60) Provisional application No. 60/458,171, filed on Mar. 26, 2003.

(51) Int. Cl.
| | |
|---|---|
| *G05B 11/01* | (2006.01) |
| *G05B 15/00* | (2006.01) |
| *G09G 5/00* | (2006.01) |
| *G06F 19/00* | (2006.01) |
| *A61B 5/103* | (2006.01) |
| *G06G 7/48* | (2006.01) |

(52) U.S. Cl. .................... 345/156; 318/560; 463/30; 600/595; 700/260; 700/262; 700/264; 703/7

(58) Field of Classification Search ......... 345/156–183, 345/184; 318/560, 568.1–568.25, 575; 463/30; 600/595; 700/260–264; 703/7
See application file for complete search history.

(56) References Cited

U.S. PATENT DOCUMENTS 4,280,605 A  *  7/1981  Papadopoulos .......... 192/223.3
5,248,960 A       9/1993  Hamma ...................... 345/157

(Continued)

FOREIGN PATENT DOCUMENTS

JP       2006-024041       1/2006

OTHER PUBLICATIONS

Berkelman et al. "Design of a Hemispherical Magnetic Levitation Haptic Interface," 1996 ASME Mechanical Engineering Congress and Exposition, Atlanta, Nov. 17-22, 1996, DSC-vol. 58 pp. 483-488.

(Continued)

*Primary Examiner*—Alexander S. Beck
(74) *Attorney, Agent, or Firm*—Seed IP Law Group PLLC

(57) ABSTRACT

A haptic device for human/computer interface includes a user interface tool coupled via cables to first, second, third, and fourth cable control units, each positioned at a vertex of a tetrahedron. Each of the cable control units includes a spool and an encoder configured to provide a signal corresponding to rotation of the respective spool. The cables are wound onto the spool of a respective one of the cable control units. The encoders provide signals corresponding to rotation of the respective spools to track the length of each cable. As the cables wind onto the spools, variations in spool diameter are compensated for. The absolute length of each cable is determined during initialization by retracting each cable In turn to a zero length position. A sensor array coupled to the tool detects rotation around one or more axes.

49 Claims, 6 Drawing Sheets

U.S. PATENT DOCUMENTS

| | | | | |
|---|---|---|---|---|
| 5,305,429 | A | * | 4/1994 | Sato et al. .................... 345/419 |
| 5,389,865 | A | | 2/1995 | Jacobus et al. ......... 318/568.11 |
| 5,440,476 | A | * | 8/1995 | Lefkowitz et al. ............. 700/56 |
| 5,576,727 | A | | 11/1996 | Rosenberg et al. .......... 345/179 |
| 5,577,981 | A | | 11/1996 | Jarvik ........................... 482/4 |
| 5,587,937 | A | * | 12/1996 | Massie et al. ................... 703/7 |
| 5,709,219 | A | | 1/1998 | Chen et al. .................. 128/782 |
| 5,828,813 | A | | 10/1998 | Ohm ........................... 395/95 |
| 6,104,380 | A | * | 8/2000 | Stork et al. .................. 345/158 |
| 6,281,651 | B1 | | 8/2001 | Haanpaa et al. ......... 318/568.11 |
| 6,385,509 | B2 | | 5/2002 | Das et al. .................... 700/260 |
| 6,394,998 | B1 | | 5/2002 | Wallace et al. ................. 606/1 |
| 6,413,229 | B1 | | 7/2002 | Kramer et al. .............. 600/595 |
| 6,417,638 | B1 | | 7/2002 | Guy et al. .................... 318/560 |
| 6,587,749 | B2 | * | 7/2003 | Matsumoto ................. 700/245 |
| 6,630,923 | B2 | | 10/2003 | Sato ............................ 345/156 |
| 6,704,001 | B1 | * | 3/2004 | Schena et al. ............... 345/161 |
| 6,879,315 | B2 | * | 4/2005 | Guy et al. .................... 345/156 |
| 7,404,716 | B2 | | 7/2008 | Gregorio et al. |
| 2001/0038376 | A1 | | 11/2001 | Sato ............................ 345/156 |
| 2008/0150891 | A1 | | 6/2008 | Berkley et al. |

OTHER PUBLICATIONS

Bouguila et al., "New Haptic Device for Human-Scale Virtual Environment: Scaleable-SPIDAR," International Conference on Artificial Reality and Tele-Existence (ICAT97), Tokyo, Japan, pp. 93-98. 1997.

Brooks, et al., "Project Grope—Haptic Displays for Scientific Visualization," Computer Graphics 24(4):177-185, 1990.

Fabiani et al., Human Interface Using the Rutgers Master II Force Feedback Interface, Proceedings of VRAIS'96, pp. 54-59.

Gomez et al., "Integration of the Rutgers Master II in a Virtual Reality Simulation," Proceedings of the Virtual Reality Annual International Symposium (VRAIS '95), pp. 198-202.

Inoue et al., "A New Force Computation Method for Wire Driven Force Display," The Institute of Image Information and Television Engineers, HIR 2001-54, NIM 2001-63, 6 pages.

Ishii et al, "A 3D Spatial Interface Device Using Tensed Strings," Presence, vol. 3 No. 1, Winter 1994, pp. 81-86.

Ishii et al., "Networked SPIDAR: A Networked Virtual Environment with Visual, Auditory, and Haptic Interaction," Presence, vol. 3 No. 4, Fall 1994, pp. 351-359.

Iwata, "Artificial Reality with Force-feedback: Development of Desktop Virtual Space with Compact Master Manipulator," Computer Graphics, vol. 24, No. 4, Aug. 1990, pp. 165-170.

Kawamura et al., "A New Type of Master Robot for Teleoperation Using a Radial Wire Drive System," Proceedings of the 1993 IEEE/RSJ International Conference on Intelligent Robots and Systems, Yokohama, Japan, pp. 55-60, 1993.

Kawamura et al., "Development of an Ultrahigh Speed Robot FALCON using Wire Drive Systems," IEEE International Conference on Robotics and Automation, pp. 215-220, 1995.

Kim et al., "Personal VR system for rehabilitation to hand movement," ICAT'98, pp. 102-108.

Kim, "A Proposal of 7 DOFs Force Display: SPIDAR-G", Ph.D dissertation, Tokyo Institute of Technology, Dec. 2004, 102 pages.

Kushida et al., "A Proposal of Free Form Modeling Method Based on Glass-work Metahphor," The Institute of Electronics, Information and Communication Engineers, Technical Report of IEICE, MVE2000-33 (Jun. 2006), pp. 11-17.

Massie, "Design of a Three Degree of Freedom Force-Reflecting Haptic Interface," Bachelor of Science Thesis, Massachusetts Institute of Technology, 39 pages, 1993.

MPB Technologies Inc., "6 DOF Haptic Interface," retrieved Feb. 22, 2010, from http://www.mpb-technologies.ca/mpbt/mpbt_web_2009/_en/6dof/index.html, 5 pages.

MPB Technologies Inc., "7 DOF Haptic Interface," retrieved Feb. 22, 2010, from, http://www.mpb-technologies.ca/mpbt/mpbt_web_2009/_en/7dof/features.html, 4 pages.

Sato et al., "A Proposal of 7 DOF Force Display Using 8 Strings", The Institute of Image Information and Television Engineers, HIR2000-100, NIM2000-100, 6 pages.

Sato et al., "Space Interface Device for Artificial Reality—SPIDAR," Systems and Computers in Japan, vol. 23, No. 12, pp. 44-54, 1992, Translated from Denahi Joho Tsushin Gakkai Ronbunshi, vol. 74-D-II, No. 7, Jul. 1991, pp. 887-894.

Turner et al., "Preliminary Tests of an Arm-Grounded Haptic Feedback Device in Telemanipulation," Proceedings of the ASME IMECE Haptics Symposium, Anaheim, CA, Nov. 1998, 5 pages.

Walairacht et al., "Two-Handed Multi-Fingers String-Based Haptic Interface Device," IEICE Trans. Inf. & Syst., vol. E 84-D, No. 3 Mar. 2001, pp. 365-373.

CyberGlove II, URL=http://www.cyberglovesystems.com/products/cyberglove-ii/overview, download date Aug. 9, 2010, 1 page.

Hashimoto et al., "Intuitive and Effective 3-D Modeler in CAVE," IEIC Technical Report 99(184):9-16, 1999 (English Abstract only).

Hashimoto et al., "Development of Haptic Device on a Human-Scale Virtual Reality Environment," Human Interface 2000 Tsukuba, 2000, pp. 423-426.

Hatano et al., "Six Degree of Freedom Master Using Eight Tensed Strings," Proceedings of the Eighth International Symposium on Measurement and Control in Robotics, Jun. 8-12, 1998, Prague, Czechoslovakia, pp. 251-255.

Iishi et al., "Force Sensations in Pick-and-Place Tasks," Dynamic Systems and Control—ASME 1994, DSC-vol. 55-1, pp. 339-344.

Ottensmeyer et al., "Input and Output for Surgical Simulation: Devices to Measure Tissue Properties in vivo and a Haptic Interface for Laparoscopy Simulators," Medicine Meets Virtual Reality 2000, pp. 236-242.

Ben-Ur, "Development of a Force-Feedback Laparoscopic Surgery Simulator," Master's Thesis, Massachusetts Institute of Technology, Sep. 1999, 114 pages.

International Search Report, mailed Feb. 3, 2005, for PCT/US2004/009295, 1 page.

Written Opinion, mailed Feb. 3, 2005, for PCT/US2004/009295, 4 pages.

"The Phantom Haptics Interfaces: A Device for Probing Virtual Objects," SensAble Technologies, http://www.sensable.com/community/asme.htm, download date of Nov. 16, 2006. (The Phantom Arm '93).

"Industrial Controls", Immersion Corporation, http://www.immersion.com/industrial/joystick/impulse_engine.php, download date of Nov. 16, 2006.

"CyberGrasph™ Exoskeleton" Immersion Corporation—3D Interaction: Products, http://www.immersion.com/3d/products/cyber_grasph.php, download date of Nov. 16, 2006.

CyVerse Corp., "Spidar (CyDar) Incormation", http://www.cyverse.co.jp/eng/ and http://www.cyverse.co.jp/Products/spidar.html, download dates of Nov. 16, 2006.

Jackson et al., "Force Feedback and Medical Simulation," Interactive Technology and the New Paradigm for Healthcare, IOS Press and Ohmsha, 1995, pp. 147-151.

Kim et al., "Haptic Interface with 7 DOF Using 8 Strings: SPIDAR-G," ICAT2000, Oct. 25-27, 2000, National Taiwan University, Tawain, 7 pages.

Kim et al, "Design of a Tension Based Haptic Interface SPIDAR-G," 4$^{th}$ World Multiconference on Systemics, Cybernetics and Informatics (SCI2000) and the 6$^{th}$ Internation Conference on Information Systems Analysis and Synthesis (ISAS2000), Orando, FL, USA, in Jul. 23-26, 2000, 6 pages.

Kim et al., "Development of Tension Based Haptic Interface and Possibility of its Application to Virtual Reality," VRST2000, Oct. 22-25, 2000, Seoul, Korea, pp. 199-205.

Kim et al., "Design of a Tension Based Haptic Interface SPIDAR-G," IMECE2000 (joint with ASME2000), DSC-vol. 69-2, Proceedings of the ASME, Nov. 5-10, 2000, Orlando, FL, USA, 4 pages.

Kim et al., "'Cutting Edge' Force-Feedback Device : SPIDAR-G," Proceedings of the 32$^{nd}$ ISR (International Symposium on Robotics), Apr. 19-21, 2001, Seoul, Korea, pp. 1771-1776.

Kim et al., "Tension Based 7-DOF Force Feedback Device: SPIDAR-G," Proceedings of the IEEE Virtual Reality 2002, Mar. 24-28, 2002, Orlando, FL, USA, 2 pages.

Kim et al., "Tension Based 7 DOFs Force Feedback Devices: SPIDAR-G," Transactions on Control, Automation, and Systems Engineering vol. 4, No. 1, Mar. 2002, pp. 9-16.

Kim et al., "A Novel Seven Degree of Freedom Haptic Device for Engineering Design," Journal of Virtual Reality, Springer-Verlag London Ltd., UK, 2003, pp. 217-228.

* cited by examiner

METHOD, APPARATUS, AND ARTICLE FOR FORCE FEEDBACK BASED ON TENSION CONTROL AND TRACKING THROUGH CABLES

BACKGROUND OF THE INVENTION

1. Field of the Invention

The disclosure is generally related to haptic systems employing force feedback.

2. Description of the Related Art

Touch, or haptic interaction is a fundamental way in which people perceive and effect change in the world around them. Our very understanding of the physics and geometry of the world begins by touching and physically interacting with objects in our environment. The human hand is a versatile organ that is able to press, grasp, squeeze or stroke objects; it can explore object properties such as surface texture, shape and softness; and it can manipulate tools such as a pen or wrench. Moreover, touch interaction differs fundamentally from all other sensory modalities in that it is intrinsically bilateral. We exchange energy between the physical world and ourselves as we push on it and it pushes back. Our ability to paint, sculpt and play musical instruments, among other things depends on physically performing the task and learning from the interactions.

Haptics is a recent enhancement to virtual environments allowing users to "touch" and feel the simulated objects with which they interact. Haptics is the science of touch. The word derives from the Greek haptikos meaning "being able to come into contact with". The study of haptics emerged from advances in virtual reality. Virtual reality is a form of human-computer interaction (as opposed to keyboard, mouse and monitor) providing a virtual environment that one can explore through direct interaction with our senses. To be able to interact with an environment, there must be feedback. For example, the user should be able to touch a virtual object and feel a response from it. This type of feedback is called haptic feedback.

In human-computer interaction, haptic feedback refers both to tactile and force feedback. Tactile, or touch feedback is the term applied to sensations felt by the skin. Tactile feedback allows users to feel things such as the texture of virtual surfaces, temperature and vibration. Force feedback reproduces directional forces that can result from solid boundaries, the weight of grasped virtual objects, mechanical compliance of an object and inertia.

Tactile feedback, as a component of virtual reality simulations, was pioneered at MIT. In 1990 Patrick used voice coils to provide vibrations at the fingertips of a user wearing a Dextrous Hand Master Exoskeleton. Minsky and her colleagues developed the "Sandpaper" tactile joystick that mapped image texels to vibrations (1990). Commercial tactile feedback interfaces followed, namely the "Touch Master" in 1993, the CyberTouch® glove in 1995, and more recently, the "FEELit Mouse" in 1997.

Scientists have been conducting research on haptics for decades. Goertz at Argonne National Laboratories first used force feedback in a robotic tele-operation system for nuclear environments in 1954. Subsequently the group led by Brooks at the University of North Carolina at Chapel Hill adapted the same electromechanical arm to provide force feedback during virtual molecular docking (1990). Burdea and colleagues at Rutgers University developed a light and portable force feedback glove called the "Rutgers Master" in 1992. Commercial force feedback devices have subsequently appeared, such as the PHANTOM™ arm in 1993, the Impulse Engine in 1995 and the CyberGrasp® glove in 1998.

Haptic devices (or haptic interfaces) are mechanical devices that mediate communication between the user and the computer. Haptic devices allow users to touch, feel and manipulate three-dimensional objects in virtual environments and tele-operated systems. Most common computer interface devices, such as basic mice and joysticks, are input-only devices, meaning that they track a user's physical manipulations but provide no manual feedback. As a result, information flows in only one direction, from the peripheral to the computer. Haptic devices are input-output devices, meaning that they track a user's physical manipulations (input) and provide realistic touch sensations coordinated with on-screen events (output). Examples of haptic devices include consumer peripheral devices equipped with special motors and sensors (e.g., force feedback joysticks and steering wheels) and more sophisticated devices designed for industrial, medical or scientific applications (e.g., PHANTOM™ device).

Haptic interfaces are relatively sophisticated devices. As a user manipulates the end effecter, grip or handle on a haptic device, encoder output is transmitted to an interface controller at very high rates. Here the information is processed to determine the position of the end effecter. The position is then sent to the host computer running a supporting software application. If the supporting software determines that a reaction force is required, the host computer sends feedback forces to the device. Actuators (motors within the device) apply these forces based on mathematical models that simulate the desired sensations. For example, when simulating the feel of a rigid wall with a force feedback joystick, motors within the joystick apply forces that simulate the feel of encountering the wall. As the user moves the joystick to penetrate the wall, the motors apply a force that resists the penetration. The farther the user penetrates the wall, the harder the motors push back to force the joystick back to the wall surface. The end result is a sensation that feels like a physical encounter with an obstacle.

The human sensorial characteristics impose much faster refresh rates for haptic feedback than for visual feedback. Computer graphics has for many years contented itself with low scene refresh rates of 20 to 30 frames/sec. In contrast, tactile sensors in the skin respond best to vibrations that are more than an order-of-magnitude higher than visual rates. This order-of-magnitude difference between haptics and vision bandwidths often requires that the haptic interface incorporate a dedicated controller. Because it is computationally expensive to convert encoder data to end effecter position and translate motor torques into directional forces, a haptic device will often have its own dedicated processor. This removes computation costs associated with haptics and the host computer can dedicate its processing power to application requirements, such as rendering high-level graphics.

General-purpose commercial haptic interfaces used today can be classified as either ground-based devices (force reflecting joysticks and linkage-based devices) or body-based devices (gloves, suits, exoskeletal devices). The most popular design on the market is a linkage-based system, which consists of a robotic arm attached to a grip (usually a pen). A large variety of linkage based haptic devices have been patented (examples include U.S. Pat. Nos. 5,389,865; 5,576,727; 5,577,981; 5,587,937; 5,709,219; 5,828,813; 6,281,651; 6,413,229; 6,417,638). The arm tracks the position of the grip and is capable of exerting a force on the tip of this grip. To meet the haptic demands required to fool one's sense of touch, sophisticated hardware and software are required to determine the proper joint angles and torques necessary to exert a single point of force on the tip of the pen. Not only is it difficult to control force output because of the update demand, the mass of a robotic arm introduces inertial forces that must be accounted for.

An alternative to a linkage-based device is one that is tension-based. Instead of applying force through links, cables are connected a point on a "grip" in order to exert a vector force on that grip. Encoders can be used to determine the lengths of the connecting cables, which in turn can be used to establish position of the cable connection point on the grip. Motors are used to create tension in the cables, which results in an applied force at the grip. There is only one commercial tension based device available, through a Japanese company called Cyverse.

The SPIDAR-G is a 7 degree of freedom haptic device that allows translational, rotational and grip force. This design resulted from Dr. Seahak Kim's PhD work (Dr. Seahak Kim is currently an employee of Mimic Technologies, Inc.). References for much of Dr. Seahak Kim's work on the SPIDAR-G have been listed above.

Predating Dr. Seahak Kim's work on the SPIDAR-G, Japanese Patent No. 2771010 and U.S. Pat. No. 5,305,429 were filed that describe a "3D input device" as titled in the patent. This system consists of a support means, display means and control means. The support means is a cubic frame. Attached to the frame are 4 encoders and magnetic switches capable of preventing string movement over a set of pulleys. The pulleys connect the tip of each encoder to strings that are wound through the pulleys. Each string continues out of the pulley to connect with a weight that generates passive tension in the string. The ON/OFF magnetic switches allow the strings to be clamped on command from the host computer. The strings connect to the user's fingertip, which are connected to the weights through the pulleys. The user moves his or her fingertip to manipulate an "instruction point" in a virtual environment, which is displayed through a monitor. As the user moves his or her fingertip, the length of the four strings change, and a computer calculates a three-dimensional position based on the number of pulses from the encoder, which indicate the change of string length between the pulleys and the user's finger. If the three-dimensional position of the fingertip is found to collide with a virtual object as determined by a controlling host computer, then the ON/OFF magnetic switch is signaled to grasp some or all of the strings so that movement is resisted. Forces are not rendered in a specific direction, but resistance to movement in some or all directions indicates that a user has contacted a virtual object. When the fingertip is moved outside the boundary of a virtual object, the magnetic switch is turned off to release the strings. The user is then able to move his or her finger freely.

The "3 dimensional input device" introduced in U.S. Pat. No. 5,305,429 is not capable of controlling or rendering directional forces. It is therefore not possible to render three-dimensional forces in the manner typically associated with a haptic device. In other words, this device is not capable of simulating haptic effects such as the feel or contact with a virtual three-dimensional surface.

The "3 dimensional input device" cannot render controlled vector forces because of the following reasons, (i) it is impossible to display exact directional force, because the device can only apply drag, or resistance to movement to each string by ON/OFF magnetic switches and cannot impose an exact tension in each string; (ii) there is no accounting for the changing force applied by the weights attached to each string which provide a variable tension as the velocity of the moving weight changes the tension; (iii) there is no accounting for extraneous forces resulting from friction between the frame, pulleys, ON/OFF magnetic switches and the strings; and (iv) there is no initialization sequence described which is required for determining initial string lengths as need for determining string orientations and finger position so that forces can be reflected accurately. In summary this is not a true force feedback device, but instead is only a tracking mechanism with a single force effect (direction nonspecific drag). As an input device, the system also lacks a robust measurement method for determining the length of the strings, which results in substantial fingertip position measurement errors. There is also no means for measuring orientation of the finger (roll, pitch and yaw).

A system that combines virtual reality with exercise is described in U.S. Pat. No. 5,577,981. This system uses sets of three cables with retracting pulleys and encoders to determine the position of points on a head mounted display. Using the lengths of the three cables, the position of the point in space is found. Tracking three points on the helmet (9 cables) allows head tracking of 6 degrees of freedom. Three cables attached to motor and encoders are also used to control the movement of a boom that rotates in one dimension through a vertical slit in a wall. The boom also has a servomotor at its end, about which the boom rotates. It is claimed that the force and direction of force applied by the boom can be controlled via the cables, servo motor and computer software, but no details are provided for how this is accomplished.

Applications have been filed for patents in Japan and the US to support the SPIDAR-G (as discussed earlier). This apparatus was titled "three-dimensional input apparatus" and was filed under patent No. 2001-282448 in Japan, and a U.S. patent application has also been submitted: No. 20010038376. This device also consists of a support means, display means and control means similar to that described in U.S. Pat. No. 5,305,429. However, this device uses "at least seven strings" to accommodate "at least six degrees of freedom" (actually the patent application only explains 7 degrees of freedom with 8 strings, but a claim is made for 6 degrees of freedom with seven strings). The mentioned support means includes a cubic frame, where a motor and encoder are attached to at least seven locations on the frame. The tip of each encoder is connected to a spool on a motor, and this spool winds the string. The encoder and motor are rotated simultaneously. The motors are meant to create tension in the strings in place of the weights used in the earlier patent. Instead of the string attaching to the users finger, the strings attach to a sphere shaped grip.

This grip has a mechanical structure that consists of two poles that are rotated based on the grasp force between the thumb and other fingers of the user. Two strings are connected to each of the four extremities of the two poles. If the user moves the tool to manipulate a virtual object in a virtual environment, as displayed through a monitor, each string length is changed, and the computer is used to calculate a three dimensional position (translation, rotation and grasp information) based on the number of pulses from the encoder, which is an indication of a change in string length. If contact is made with a virtual object, the controlling computer is used to calculate the tensions in the strings that are necessary to render force and torque at the grip.

The system described in Japanese patent 2001-282448 can therefore actively display translation, rotation, and grasp force. As a result, the user is able to "touch" virtual objects through the display of force. However, the above-mentioned "3 Dimensional interface device" requires at least seven strings to determine position and render force, even if rotation and grip forces are not being applied, and, while the design described above is adequate for displaying seven degrees of force feedback, there are severe limitations imposed if less than seven degrees of force feedback are required.

BRIEF SUMMARY OF THE INVENTION

In one aspect of the invention, an input/output haptic interface is provided, to input the position of a tool(s) held by the user to a computer by directly determining position and orientation of the tool in a three-dimensional space. Tracking may be accomplished over as many as six degrees of freedom.

In another aspect, a method is provided, for determining a tool position through cable lengths with minimal error. Position of the tool may also be established with alternative tracking mechanisms such as through infrared, electromagnetic, gyro or acceleration sensors.

In another aspect, an input/output haptic interface is provided, to render forces to a point on a tool held by a user over two or three dimensions as signaled from software running on a host computer. Multiple sets of cables render vector forces to multiple points on a tool. Alternatively, multiple sets of cables render vector forces to points on multiple tools used in the same workspace.

In yet another aspect, a new calibration system is provided, for maintaining tool position accuracy with minimal user intervention, even after powering down and reactivation of the apparatus over multiple iterations.

In a further aspect, an input/output haptic interface provides a user with the "touch" sensation generated as a result of interaction with virtual environments, which could include force effects such as contact force resulting from tool collision with rigid or deformable virtual surfaces, the pull, push, weight or vibration of a virtual object contacting a tool(s), and/or viscous resistance and inertia experienced as a tool moves through virtual fluid.

In still a further aspect, an interface relays position and forces data to and from a robot (or similar system). Control of the robot (or similar system) through the invention can be used to establish telepresence.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

While the system described in Japanese patent 2001-282448, and outlined in the background section of this document, provides significant advantages over the previous art, there are still some problems that remain unaddressed. For example, when calculating the length of each string, error is introduced because a changing spool diameter resulting from string wrapped over itself on the spool is not accounted for; the device calculates rotation based on the length change in eight strings, where a minor error in length variation of one string can substantially affect accuracy (calculation algorithm is not robust about rotation); there is no initialization sequence provided, which is necessary for determining initial string length as required for determining position, orientation and grip, and minimizing associated error; the grip is connected with eight strings, so workspace is limited if the user wishes to avoid tangling the strings; and there is no accounting for extraneous forces resulting from friction between the frame, pulleys, motors and strings.

In the following description, certain specific details are set forth in order to provide a thorough understanding of various embodiments of the invention. However, one skilled in the art will understand that the invention may be practiced without these details. In other instances, well-known structures associated with motors, motor controllers, computers, microprocessors, memories and the like have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense, that is as "including, but not limited to."

The headings provided herein are for convenience only and do not interpret the scope or meaning of the claimed invention.

Figure 1:
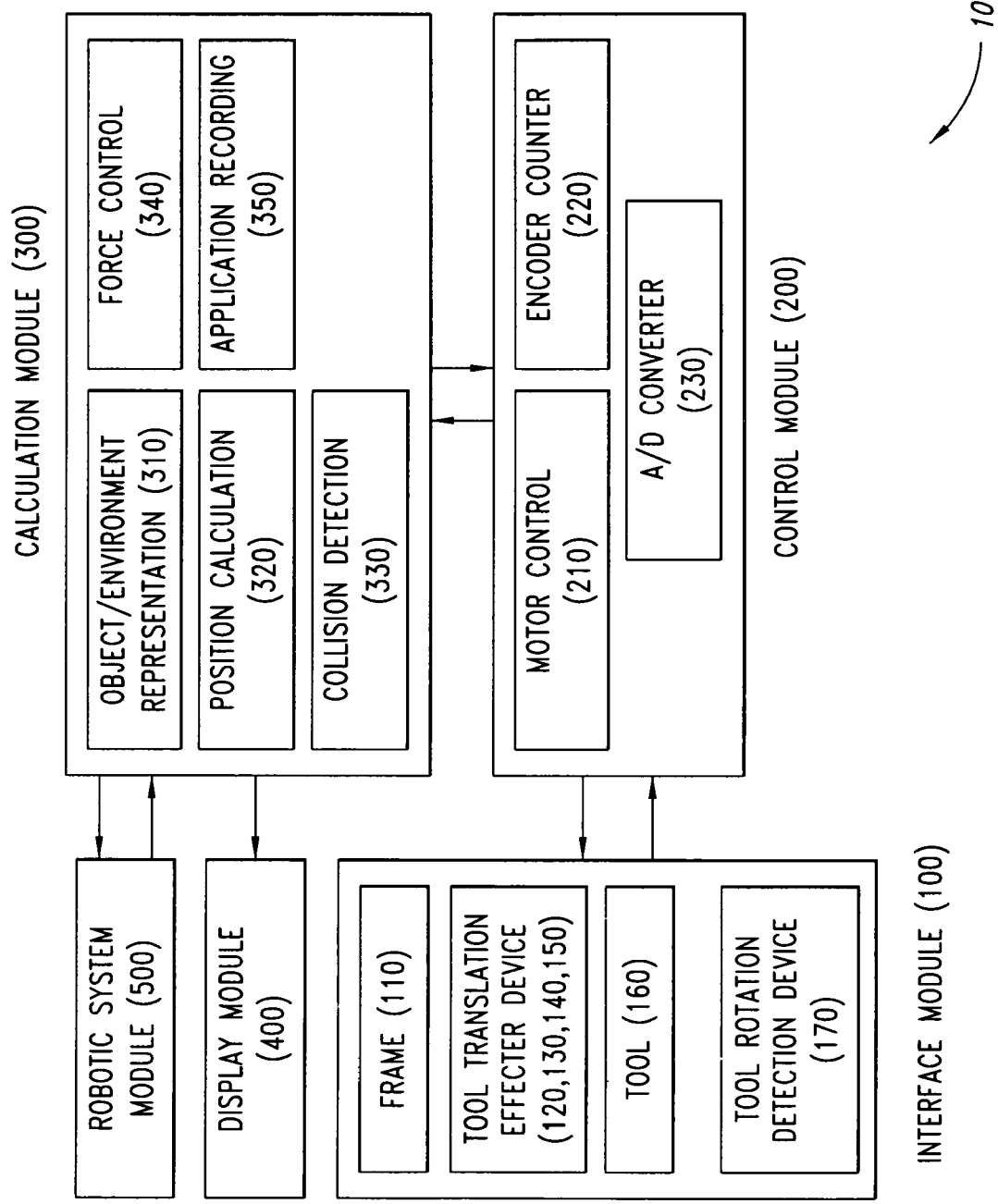
FIG. 1 is a block diagram that describes the components of the invention and how they relate to each other.

FIG. 1 shows a tension based force feedback system 10 using cables, includes a number of devices or modules, such as: an interface module 100 to detect translational and rotational signals concerning the tracking of a tool manipulated by the user; a control module 200 to convert analog and pulse signals generated from the interface device 100 to digital signals and to relay force signals to the mentioned interface device 100; a calculation module 300 to control force feedback, to calculate the position of a tool based on translation and rotational manipulation by the user, and to mathematically represent objects and/or environments that might interact with the tool; a display module 400 for the user to perceive visual and/or audible information about the tool 160 and objects and/or environments which are modeled in the calculation device 300; and a robotic module 500, which in those embodiments of the invention that are so configured, receives control instructions from, and provides feedback signals to, the calculation module 300.

Figure 2:
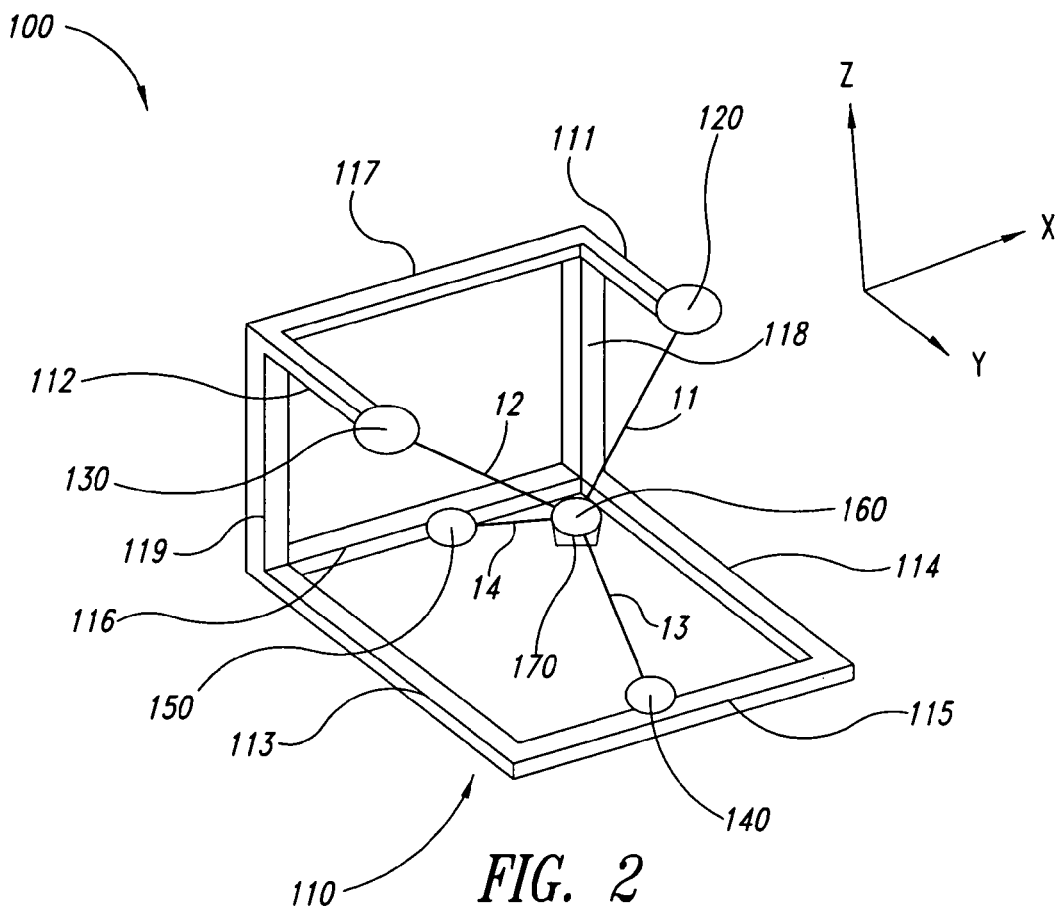
FIG. 2 is a perspective view of one possible configuration of the interface device which includes tool translation effecter components, cables and a supporting frame.

FIG. 2 shows one possible configuration of the interface device 100. This configuration of the interface device includes a frame 110, four cable control units or tool translation effecter devices 120, 130, 140, and 150, a tool 160, and a sensor array, or tool rotation detection device 170.

Reference to the tool 160 may also be construed to refer to a connection point to which the cables 11, 12, 13, and 14 are attached. According to some embodiments of the invention, a separate tool, device, handle, or other implement is coupled to the tool 160.

The frame 110 in FIG. 2 represents one possible structure for supporting the tool translation effecter devices 120, 130, 140, and 150 and the other components that are located within a three dimensional space. The frame 110 can be constructed from a variety of materials, such as sheet metal, trusses or rigid plastic, and can take the form of a wide variety of geometries that partially enclose a three dimensional volume. The main requirement of the frame is to provide rigid support of elements such as the detection devices 120, 130, 140, and 150. At the same time the frame geometry should allow the user to freely manipulate the tool 160 within a prescribed workspace, without excessive collision of the tool 160, or the user's hands, with the frame 110. In the embodiment illustrated in FIG. 2, the prescribed workspace is approximately cubic with the volume partially enclosed by sides 111-119.

Each tool translation effecter device 120, 130, 140 and 150 is positioned in three-dimensional space, and coupled at a corresponding anchor point to the frame 110. In the embodiment of FIG. 2, the tool translation effecter device 120 is positioned at the end of the upper right arm on the frame side 111, the tool translation effecter device 130 is positioned at the end of the upper left arm on the frame side 112, the tool translation effecter device 140 is positioned at the lower front of the frame in the center of side 115, and the tool translation effecter device 150 is positioned at the lower back of the frame in the center of side 116. Tool translation effecter devices 120 and 130 are centered in-between the tool translation effecter devices 140 and 150 when viewed along the X-axis. Tool translation effecter devices 140 and 150 are centered in-between the tool translation effecter device 120 and 130 when viewed along the Y-axis. The tool translation effecter devices 120, 130, 140 and 150 can be positioned in a variety of configurations, and are not limited to that illustrated by FIG. 2. The main objective when placing the tool translation effecter devices 120, 130, 140 and 150 is to maximize the volume enclosed by the devices 120, 130, 140, 150 given the geometry of the frame 110.

Figure 3:
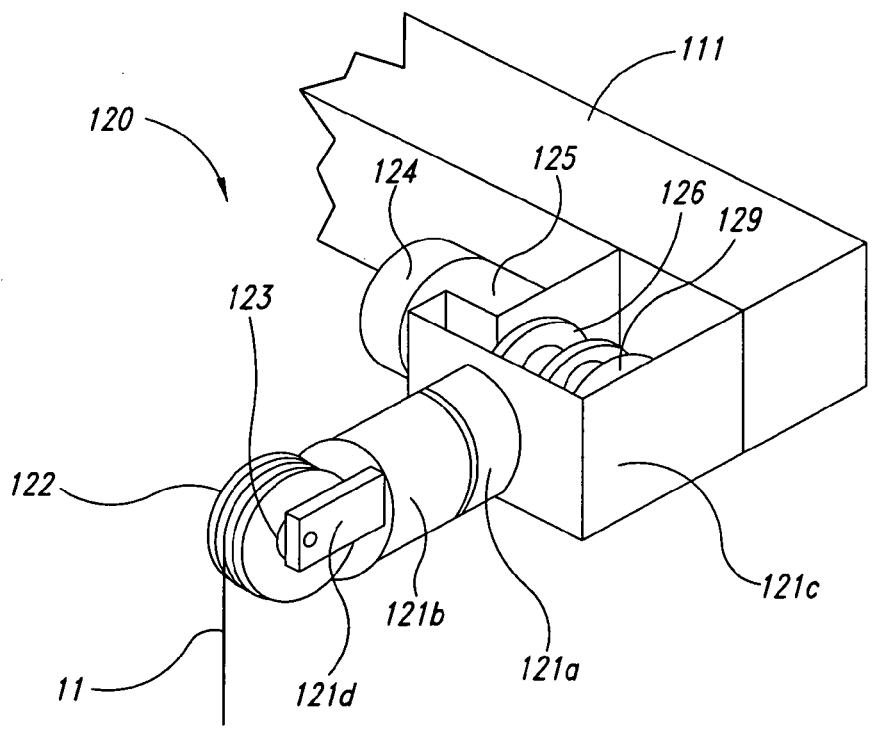
FIG. 3 is a perspective view of one possible configuration of a tool translation effecter device.
Figure 5:
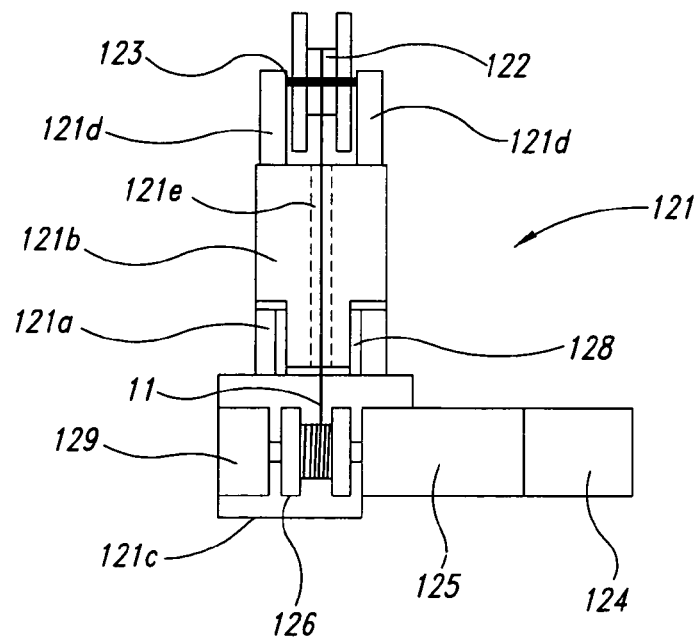
FIG. 5 is a top view of the tool translation effecter device shown in FIG. 3.
Figure 6:
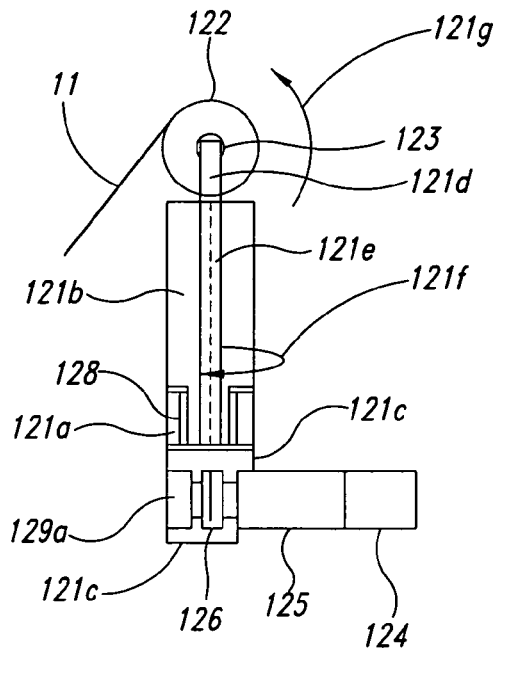
FIG. 6 is a side view of the tool translation effecter device shown in FIG. 3.

FIG. 3, 5 and 6 show detailed views of an illustrative one of the tool translation effecter devices 120, 130, 140, 150. While translation effecter device 120 is described for the purpose of illustration, it will be understood that, according to one embodiment of the invention, translation effecter devices 130, 140, and 150 are substantially identical in structure and operation.

The illustrated tool translation effecter 120 includes a mounting system 121, a pulley 122, a first bearing 123, a motor 124, an encoder 125, a spool 126, a cable 11, a second bearing 128, and a motor brake 129.

The four tool translation effecter devices 120, 130, 140 and 150 of FIG. 2 are oriented so that spools 126 generally guide the cables 11, 12, 13 and 14 toward the tool 160 with the objective of minimizing friction in the cable run (i.e., path) to the tool 160.

The mounting system 121 of each tool translation effecter 120, 130, 140, 150 provides a path that guides the cable 11 from the spool 126 to the pulley 122, while providing stability for the spool 126 and the pulley 122, so that the center of the axis of each stays fixed in position when tension is applied to the cable 11. The mounting system 121 also provides a structure to couple the respective tool translation effecter device 120, 130, 140, 150 to the frame 110. The mounting system 121 also positions the pulley 122 away from both the frame 110 and the spool 126 in a manner that enables ideal use of tool workspace. The mounting system 121 may vary in size or geometry depending on workspace requirements.

The mounting system 121 includes a link 121a that is fixed to a bracket 121c. A rotary fulcrum 121b is attached to link 121a through a secondary bearing 128. The rotary fulcrum 121b can rotate about an axis that is perpendicular to the adjacent face of link 121a. The secondary bearing between link 121a and rotary fulcrum 121b allows smooth rotation around an axis defined by hole 121e of FIG. 5 as illustrated by arrow 121f (see FIG. 6). The hole 121e runs through the center of the rotary fulcrum 121b, and the cable 11 passes through the hole 121e. The cable 11 is guided to the pulley 122 from the spool 126 through the hole 121e. The pulley 122 is mounted to the rotary fulcrum through bracket 121d. The pulley 122 rotates around bearing 123 as illustrated by arrow 121g (FIG. 6), which lies between bracket 121d and the pulley 122. In addition to its attachment to link 121a, bracket 121c is attached to the motor 124, the brake 129, and also to the frame 110.

Each motor 124 is typically a DC motor that displays minimal back drive friction. The shaft of each motor 124 is drivingly coupled to a spool 126, which is in turn coupled to a cable 11. When the motor 124 turns the respective pulley 126, the cable 11 wraps or unwraps around the pulley 126. Tension occurs in each cable 11, 12, 13 and 14 because the cables 11, 12, 13 and 14 pull at the tool 160 in opposing directions. The tension applied to each cable 11, 12, 13 and 14 is based on the torque applied by the motors 124 to the spool 126 as governed by the control device 200. In order to reduce backlash, a gear is not used, however some embodiments may include a gear where suitable.

Figure 7:
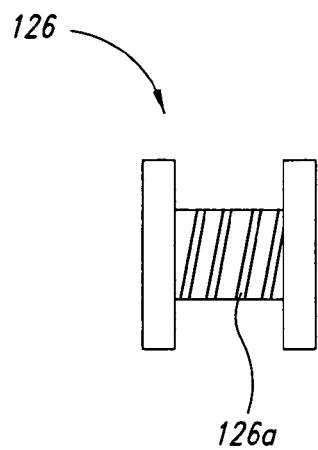
FIG. 7 shows the grooves on the second pulley of the tool translation effecter device that help evenly guide a winding cable.

An encoder 125 is coupled to each motor 124 and converts the user's manipulation as represented by rotation of the motor shaft into electrical pulses that are sent to the control device 200. Typically, an optical encoder is used with a resolution of 1024 pulses per rotation of the motor shaft. However, a variety of optical encoders can be used that have a wide range of resolutions. An encoder is therefore chosen based on application requirements and price constraints. Determining translational movement of the tool 160 can be calculated from the length of each cable 11, 12, 13 and 14, which is determined from encoder 124 pulse signals. There is a mathematical relationship between cable length change, diameter of the spool 126, and the pulses per rotation. The spool 126 can be made of a variety of materials, such as aluminum, steel, rigid plastic or any other stiff material. The spool 126 may be grooved as shown in FIG. 7, allowing the cable to wrap evenly about spool 126, although such is not required.

Figure 4:
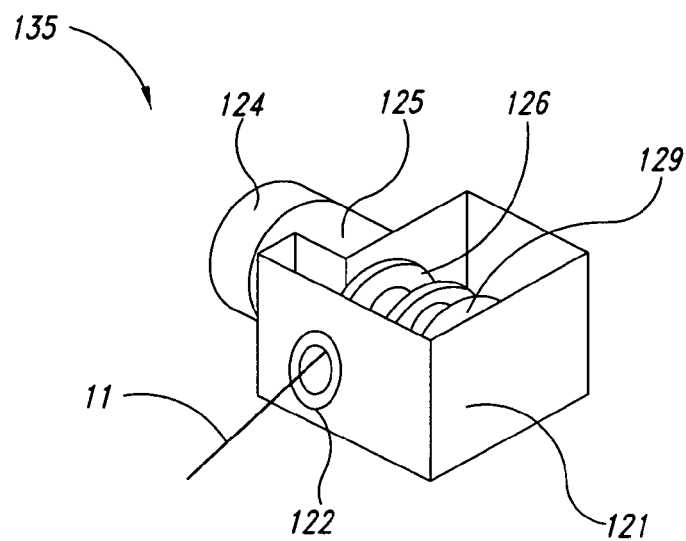
FIG. 4 is a perspective view of another possible configuration of a tool translation effecter device that uses an eyelet rather than a pulley and associated parts.

FIG. 4 shows, according to an alternative embodiment, a cable control unit 135, wherein the pulley 122, the first bearing 123, the second bearing 128, and parts 121a, 121b and 121d (shown in FIG. 3) are omitted. In the place of these components is a low friction eyelet 122 that guides the cable 11 from the spool 126 through the mounting system 121. The cable control unit 135 has fewer moving parts than the cable control unit 120 described with reference to FIGS. 3, 5, and 6, but may, in some applications, introduce more drag to the associated cable 11.

Figure 8:
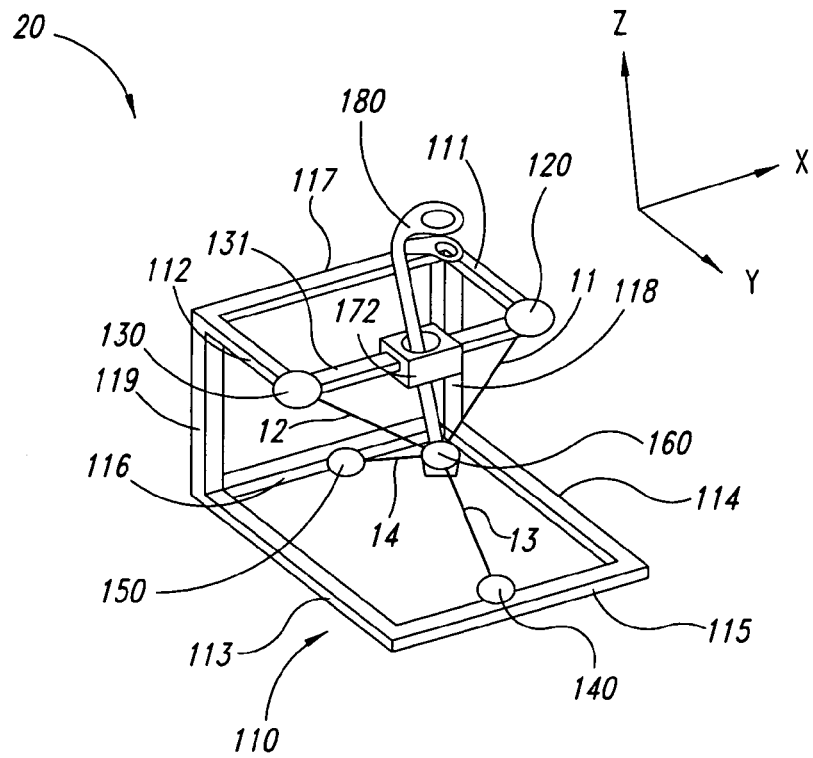
FIG. 8 is a perspective view of another possible configuration of the interface device, which includes tool translation effecter components, cables, a supporting frame, a port and a minimally invasive othoscope.

The cables 11, 12, 13 and 14 connect between the spools 126 of the tool translation effecters to the tool 160. The cables 11, 12, 13 and 14 are ideally made of a material that is substantially inelastic under tension, such as Dacron fishing line, but any string, wire or other cable that is flexible, durable and exhibits minimal stretch under tension can be used. The cables 11, 12, 13 and 14 connect to a point, or series of points in close proximity, on the tool 160 or tool holder. The tool 160 might be a stylus, pen, pliers, wrench, forceps, needle holder, scalpel, endoscope, arthroscope, minimally invasive surgical tool or other mechanical or medical tool. The tool could be free floating as illustrated in FIG. 2, or might move through a pivot point, such as the port 172 as illustrated in FIG. 8, or the port 174 of FIG. 11. Any object that can be connected to the cables 11, 12, 13 and 14, such that the cables 11, 12, 13 and 14 can apply vector forces to a point, or series of points in close proximity, on the object through cable tension, may be considered the tool 160 as used herein. The cables 11, 12, 13, 14, apply a vector force to the tool 160.

According to an embodiment of the invention, the tool 160 also carries a sensor array 170 having one or more sensors, such as gyro sensors, acceleration sensors, infrared or electromagnetic sensors that can relay signals to the control module 200. The purpose of these sensors is to relay information that can be used to determine tool orientation (roll, pitch and yaw) at the control module 200. Such sensors can also be used to relay information about the tool translation in the x, y and/or z directions in three dimensional space instead of, or in addition to, the encoders 124 to determine the cable 11, 12, 13, and 14 lengths. Such sensors are commercially available from a wide variety of vendors and take a wide variety of shapes and configurations, so the details of these sensors have not been illustrated in the figures. The wires and/or wireless transmitters/receivers for to transferring sensor signals from the sensor array 170 to the control module 200 are also not shown in the figures, although in at least one embodiment the cables 11, 12, 13, 14 may carry such signals.

As has been previously explained, according to some embodiments of the invention the tool 160 comprises a connection point to which the cables 11, 12, 13, and 14 are attached. A separate tool or device may then be coupled to the tool 160. Accordingly, the sensor array 170 may be configured to detect rotation of the separate tool, as it moves or rotates in one or more axes within the tool 160.

According to another embodiment, the tool 160 includes a vibrating element attached, whose frequency and magnitude of vibration are regulated by the control module 200. The vibration element may be used to create tactile effects. Vibration can also be used to simulate different materials. For example, a dissipating vibration signal at a high frequency might be used when simulating contact with steel as compared to a dissipating vibration signal at a lower frequency, which could be used when simulating contact with wood. Suitable vibrating elements are generally known, such as those employed in paging devices and cellular phones, so will not be discussed in detail in the interest of brevity.

The control module 200 sends control signals to the motors 124 and receives signals from the encoders 125 of each tool translation effecter device 120, 130, 140, 150. The control module 200 includes three primary components; a motor controller 210, which controls tension in each cable 11, 12, 13 and 14 via the motors 124 as directed by the calculation module 300; an encoder counter 220 that receives and counts pulse signals from the encoders 125 and provides these counts to the calculation module 300; and an A/D converter 230 that converts analog signals transmitted from each tool translation effecter device 120, 130, 140, 150 to digital signals that are relayed between the calculation module 300 and the control module 200.

The calculation module 300 consists of a local processor, memory storage and associated components on a printed circuit board for implementing local software control. The calculation module 300 may also include a remote computer, such as a conventional Pentium processor type or workstation with conventional memory and storage means. The remote computer may transfer data to the local processor through connections such as USB, serial, parallel, Ethernet, Firewire, SCSI, or any other means of transferring data at a high rate. The calculation module 300 processes information via software control. The functions of the calculation module 300 may be classified into five parts or functions: an object/environment representation function 310, a position calculation function 320, a collision detection function 330, a force control function 340, and an application recording function 350.

According to an embodiment of the invention, some or all of the processing tasks, including those described with reference to the control device 200 and the calculation device 300, may be performed by a conventional system or workstation.

The object/environment representation function 310 manages and controls modeling information about virtual (or real) objects, the three dimensional environment, the tool 160, and determines the proper interaction between the objects, environment and the tool 160. The object/environment representation function 310 might also include information about a robotic module 500, information sent from the robotic module 500, and/or how movement of the tool 160 effects navigation of the robotic module 500. The visual representation of these objects is relayed from the object/environment representation function 310 to the display module 400. The position calculation function 320 determines the position of the tool 160 by processing signals from the control module 200 about translation and rotational movement of the tool 160. The collision detection function 330 determines whether a collision has occurred between modeled objects and the tool 160. This might also include the indication of existing environmental effects such as viscous resistance and inertia experienced as a tool 160 moves through virtual fluid. When the system 10 is used to control a robot associated with the robotic module 500, collisions may be collected from the robot as it collides with real objects. The force control function 340 is used to calculate tension of each cable 11 that is appropriate for rendering reaction forces that take place at the tool 160. The summation of vector forces in the cables 11, 12, 13 and 14 will equal the reaction force at the tool 160. Such forces might be the result of reaction forces collected by a robot as it interacts with real objects. The application record function 350 manages all other software interaction that takes place in an application that utilizes the system 10.

The display module 400 displays manufactured virtual objects modeled through the calculation module 300. The display module 400 might also be used to convey visual information about real objects, such as in the case of using the system 10 to control the robotic system 500 as it interacts with real objects. The display module 400 is typically understood to be a conventional video monitor type and may be, for example, NTSC, PAL, VGA, or SVGA. The display module may also consist of a head mounted display or a video projection system. The display module 400 may relay a 2D representation or a stereoscopic representation for 3D projection. The display module 400 might be used, for example, to collocate stereoscopic representations into the workspace of the system 10. This could be accomplished by placing the face of a monitor between sides 116 and 117 or the images could be projected through mirrors located at the back, bottom or top of the frame 110. Stereoscopic images may also be relayed through a head mounted display. The display module 400 may relay virtual environments where the entire environment can be classified as a rendered graphical image. The display module 400 may also transmit augmented environments where graphical rendering is overlaid onto video feeds or "see through" displays of real environments. The display module 400 could also transmit pure video of real environments, such as might be the case when the system 10 is used to control a robot operating in a real environment.

In one embodiment the system 10 performs a variety of processes. A process to establish the initial length of each cable 11, 12, 13, and 14 is achieved through processing transmitted signals between the calculation device 300 and each encoder counter device 220 and by utilizing a history of encoder pulse counts from each tool translation effecter 120, 130, 140 and 150 as stored in the calculation device 300. The system 10 performs the process of relaying position and orientation (roll, pitch and yaw) information about the tool 160 to the calculation device 300 through optical encoders and/or sensors such as gyro sensors, acceleration sensors, infrared or electromagnetic tracking mechanisms located in and/or around the tool 160. The system 10 performs the process of establishing the position and orientation (roll, pitch and yaw) of the tool 160 in three dimensional space at the calculation device 300. The system 10 performs the process of determining the position and orientation of the tool 160 with the calculation device 300 from the signals sent by the control device 200 and/or the tool 160 to the calculation device 300.

The system 10 further performs the process of establishing in the calculation device 300 a force response that is appropriate at the tool 160 based on position and orientation of the tool 160 as it relates to virtual or real objects defined at the calculation device 300. The system 10 carries out the process of determining tension values in each cable 11, 12, 13, and 14 that will deliver a force response to the tool 160 as determined at the calculation device 300, and controlling tension in each cable 11, 12, 13, and 14, by driving the motor 124 of each tool translation effecter devices 120, 130, 140, 150 based on the tension values determined in the calculation device 300. Finally, the system 10 performs the process of relaying visual and audible information to the display device 400 from the calculation device 300 about the location and orientation of the tool 160 and virtual or real objects that the tool 160 may be interacting with.

As used in the claims, the term active tension refers to a force applied in a longitudinal direction to a cable that, if it were not resisted, would result in lengthwise movement of the cable. For example, the driving motor 124 of each of the tool translation effecters 120 applies active tension to the cable, in that the motor applies a force in the form of torque to the associated spool to retract the associated cable, thereby transferring the force longitudinally along the cable. If the force is resisted, tension on the cable will be exerted, proportionate to the force applied by the motor; if the force is not fully resisted, the cable will rewind, i.e., the active tension will result in movement of the cable. If active tension applied to each of the cables of a haptic system is equal, the system will be balanced and no movement will result. By selectively varying the force applied to individual cables, a force response, as described above, will be applied, which, if not resisted by the operator, will result in movement of the tool or attachment point according to a net value of the longitudinal forces applied. Calculation of values to produce a given force response will be described in more detail later.

This is in contrast to systems such as that described in the background of this disclosure with reference, for example, to U.S. Pat. No. 5,305,429, in which a static weight applies a constant and equal tension to each of the lines, and in which the system can resist movement of the "instruction point" by application of drag, but cannot vary the longitudinal force applied by the weights so as to result in movement of the instruction point independent of force applied by the operator.

Figure 9:
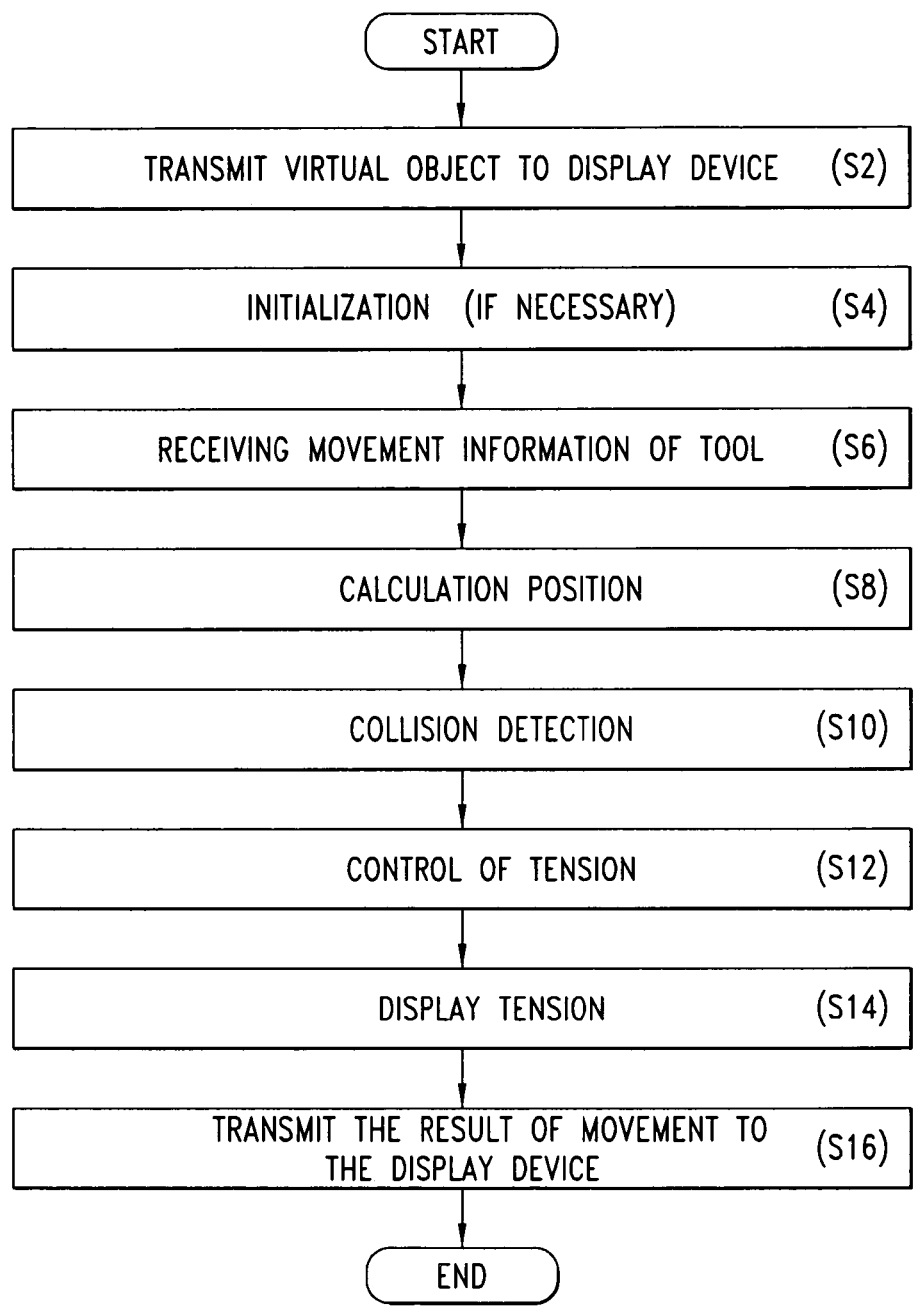
FIG. 9 shows a typical cycle of information/action flow as position of a tool is detected and force is displayed at the tool.

A typical cycle of information/action flow is shown in FIG. 9, however, there would likely be more acts or steps in the case of representing a very complex environment. The steps of FIG. 9 utilize the processes outlined above.

A process for establishing the initial length of each cable 11, 12, 13, and 14 is described below. According to one embodiment of the invention, these lengths are determined before the position of the tool 160 is calculated. Calibrating these lengths can include the following acts:

1) The point on the tool 160 where the cable 11 is attached is moved to the pulley 122 of the tool translation effecter 120 located on the upper right arm of the frame side on side 111. At this calibration point ($P_1$), the length of cable 11 extending from the pulley 122 to the tool 160 is considered to be 0 cm. The counter value of the encoder 125 of the tool translation effecter 120 is then set to 0 by the calculation device 300 while the tool 160 is in this position. The encoder counts of each tool translation effecter 120, 130, 140 and 150 are recorded at this position.

2) The point on the tool 160 where the cable 12 is attached is moved to the pulley 122 of the tool translation effecter 130 located on the upper left arm of the frame on side 112. At this calibration point ($P_2$), the length of cable 12 extending from the pulley 122 to the tool 160 is considered to be 0 cm. The counter value of the encoder 125 of the tool translation effecter 130 is then set to 0 by the calculation device 300 while the tool 160 is in this position. The encoder counts of each tool translation effecter 120, 130, 140 and 150 are recorded at this position.

3) The point on the tool 160 where the cable 13 is attached is moved to the pulley 122 of the tool translation effecter 140 located on the lower front portion of the frame on side 115. At this calibration point ($P_3$), the length of cable 13 extending from the pulley 122 to the tool 160 is considered to be 0 cm. The counter value of the encoder 125 of the tool translation effecter 140 is then set to 0 by the calculation device 300 while the tool 160 is in this position. The encoder counts of each tool translation effecter 120, 130, 140 and 150 are recorded at this position.

4) The point on the tool 160 where the cable 14 is attached is moved to the pulley 122 of the tool translation effecter 150 located on the lower back portion of the frame on side 116. At this calibration point ($P_4$), the length of cable 14 extending from the pulley 122 to the tool 160 is considered to be 0 cm. The counter value of the encoder 125 of the tool translation effecter 150 is then set to 0 by the calculation device 300 while the tool 160 is in this position. The encoder counts of each tool translation effecter 120, 130, 140 and 150 are recorded at this position.

5) There is now a relationship between the number of encoder pulses and the change in distance between the tool 160 and the pulleys 122 attached to the tool translation effecters 120, 130, 140 and 150. The method for determining cable length and the position of the tool will be described later in this document. At this point, the recorded encoder counts are adjusted to account for the fact that some pulse counts were recorded before the counter value was set to zero. Values counted before the encoder was set to zero are offset by the appropriate amount. Steps 1 through 5 can be repeated to calibrate the device if it is believed that tracking inaccuracies exist, but normally, steps 1 though 5 are only required when powering up the system 10 for the first time with a new computer.

6) When powering down the system 10, the calculation device 300 first signals for the current to be removed from each spring actuated brake 129 attached to the motor spool 126 of the tool translation effecters 120, 130, 140 and 150. This prevents the motors 124 from spinning their respective spools 126. This also keeps the encoders 125 locked in position. The calculation device 300 can then store the current pulse count from all the encoders 125 before completely powering down the system.

7) The next time the system 10 is powered up, the encoder pulse count values are then restored to each encoder 125 based on the values stored by the calculation device 300. Current to the brakes 129 is then re-established by the calculation device 300, which releases the hold on the motor spools 126. The tracking of the lengths of cables 11, 12, 13, and 14 can then resume as it did before the system 10 was last powered down.

The process to relay position, orientation and rotational information of the tool 160 to the calculation device 300 through optical encoders and/or sensors such as gyro sensors, acceleration sensors, infrared or electromagnetic tracking mechanisms located in and/or around the tool 160 will now be discussed. The optical encoders 125 of the tool translation effecter devices 120, 130, 140, 150 output analog signals that are transferred to an A/D converter 230. These signals are then converted to digital signals that are relayed to the calculation device 300 as encoder pulse counts. The digital signals are transferred to the position calculation part 320 of the calculation device 300 by way of the encoder counter part 220. The encoder pulse counts are used to determine the lengths of the cables 11, 12, 13, and 14.

The system 10 may employ a sensor array 170 having, for example, three gyro sensors or acceleration sensors to detect rotational movement of the tool 160. The sensor array 170 outputs analog signals depending on rotational acceleration or rotational degree of movement of the tool 160. The analog signals reflect rotation over three degrees of freedom (roll, pitch and yaw). These signals are transferred to A/D converter 230, which converts the signals to digital signals. The digital signals are then transferred to the position calculation part 320 of the calculation device 300 by way of the encoder counter part 220. The orientation (roll, pitch and yaw) of the tool 160 is determined based on the digital information received according to means specified by the manufacturer of the gyro sensors or acceleration sensors. Such sensors can also be used to transfer translation information about the tool 160 in a similar manner to that described above. Other sensors such as infrared or electromagnetic tracking mechanisms could likewise be used.

The process for finding tool position and orientation based on the digital information sent from the control device 200 to the calculation device 300 can be accomplished by a variety of means. In particular, there are various approaches to finding the tool position based on cable length. Some of these options are discussed in the following.

One simple approach for finding the position of the tool 160 is based on solving four equations that define cable length. These equations contain only three unknown variables, which are the tool's rectangular coordinates, x, y, and z. Equations 1 through 4 define the length $l_n$ of each cable 11, 12, 13, 14 (where n=11, 12, 13, 14), where $x_i$, $y_i$ and $z_i$ define the positions of the calibration points $P_i$ (where i=1,2,3,4) and x, y and z is the point where the cable 11, 12, 13 and 14 attach to the tool 160.

$$l_{11} = \sqrt{(x-x_1)^2 + (y-y_1)^2 + (z-z_1)^2} \qquad \text{(Eq. 1)}$$

$$l_{12} = \sqrt{(x-x_2)^2 + (y-y_2)^2 + (z-z_2)^2} \qquad \text{(Eq. 2)}$$

$$l_{13} = \sqrt{(x-x_3)^2 + (y-y_3)^2 + (z-z_3)^2} \qquad \text{(Eq. 3)}$$

$$l_{14} = \sqrt{(x-x_4)^2 + (y-y_4)^2 + (z-z_4)^2} \qquad \text{(Eq. 4)}$$

Consider the origin of the coordinate system to be in the center of the frame 110 shown in FIG. 2. Consider sides 115, 116 and 117 to be of length 2a. Consider sides 111 and 112 to be of length b and sides 113 and 114 to be 2b. Also consider sides 118 and 119 to be of length 2c.

Equations 1 through 4 can be combined to determine a solution for the tool position (as defined by coordinates x, y and z) in terms of the lengths a, b and c.

$$x = \frac{l_{12}^2 - l_{11}^2}{4a} \qquad \text{(Eq. 5)}$$

$$y = \frac{l_{14}^2 - l_{13}^2}{4b} \qquad \text{(Eq. 6)}$$

$$z = \frac{l_{14}^2 + l_{13}^2 - l_{12}^2 - l_{11}^2 + 2a^2 - 2b^2}{8c} \qquad \text{(Eq. 7)}$$

Equation 5 can be found by squaring both sides of equations 1 and 2, subtracting equation 1 from equation 2, and then by isolating the variable x. Equation 6 can be found by squaring both sides of equations 3 and 4, subtracting equation 3 from equation 4, and then by isolating the variable y. Equation 7 can be found by squaring both sides of equations 1-4, adding equations 3 and 4 and from this subtract equations 1 and 2, and then by isolating the variable z. It should be noted that only three of equations 1-4 are necessary to solve for x, y, and z, but using all four equations is a simpler approach. There are a variety of algebraic mathematical methods for solving for x, y and z given equations 1, 2, 3 and 4 and the invention is not limited to the solving method described above.

To briefly summarize another method for determining the lengths of cable 11, 12, 13 and 14, the calibrations points $P_1$, $P_2$, $P_3$, $P_4$ discussed earlier form a tetrahedral volume, V. The position of the tool 160 where the cables 11, 12, 13 and 14 are attached can be used to divide this tetrahedron volume into four smaller tetrahedrons. If P is the cable connection point to the tool 160, consider $V_1$ the volume formed by P, $P_2$, $P_3$ and $P_4$, $V_2$ the volume formed by P, $P_1$, $P_3$ and $P_4$, $V_3$ the volume formed by P, $P_1$, $P_2$ and $P_4$, and $V_4$ the volume formed by P, $P_1$, $P_2$ and $P_3$. Since we know the side lengths of all of these tetrahedrons, we can determine these volumes from the side lengths (for example using Piero della Francesca's formula or Heron's formula) where the distance between the calibration points and the tool 160 (in other words, the cable lengths) form the sides. It is then possible to use volume coordinates and shape functions to find the tool position (Zienkiewicz) as shown below.

$$x = \frac{V_1}{V}x_1 + \frac{V_2}{V}x_2 + \frac{V_3}{V}x_3 + \frac{V_4}{V}x_4 \quad \text{(Eq. 8)}$$

$$y = \frac{V_1}{V}y_1 + \frac{V_2}{V}y_2 + \frac{V_3}{V}y_3 + \frac{V_4}{V}y_4 \quad \text{(Eq. 9)}$$

$$z = \frac{V_1}{V}z_1 + \frac{V_2}{V}z_2 + \frac{V_3}{V}z_3 + \frac{V_4}{V}z_4 \quad \text{(Eq. 10)}$$

The cable lengths described in equations 1-7 are determined through the number of encoder pulses that result from spinning the spool 126 of the tool translation effecter devices 120, 130, 140, 150. Assume an encoder count of c pulses, where C represents the number counts per one complete motor shaft revolution (also known as encoder resolution). Also assume the spool 126 has a radius of r and that the groove separation 126a is d. The calibration process described earlier insures that the pulse count is zero when the cable length is zero. The pulse number increases as the cable unwraps from spool 126 of a tool translation effecter 120. Therefore, the length of each cable can be determined from the number of pulses based on equation 11, where the subscript i refers to the different tool translation effecter devices 120, 130, 140, 150 and their associated cables 11, 12, 13 and 14.

$$l_i = \frac{c_i}{C}\sqrt{(2\Pi r)^2 + d^2} \quad \text{(Eq. 11)}$$

The difficulty with relying completely on equation 11 is that it is possible for a cable 11 to become miss wrapped so that it does not perfectly follow the grooves 126a of the spool 126. The cable 11 might also end up wrapping on top of previously wrapped cable if the spool 126 width and/or radius are not great enough. This can change variables r and d of equation 11, which will introduce error if not accounted for. To address this source of error, the method described below can be employed.

$$L_{ij} = m_{ij}p_{ij} + n_{ij} \quad \text{(Eq. 12)}$$

Equation 12 relates cable length at the calibration positions $P_1$, $P_2$, $P_3$ and $P_4$ to the recorded encoder pulses obtained during the calibration process. The cable length, $L_{ij}$ is known at every calibration position $P_j$, where i refers to each of the four cables and j refers to the different calibration positions (where i=1 ... 4, j=1 ... 4 and i≠j). The number of encoder counts recorded at these lengths for the cables, $p_{ij}$, was recorded during the calibration process for calibration positions $P_1$, $P_2$, $P_3$ and $P_4$. Given the known lengths, $L_{ij}$, of the cables at each calibration position and recorded pulse counts, $p_{ij}$, the linear curve of equation 12 can be fit to the data and variables $m_{ij}$ and $n_{ij}$ can be solved. Methods, such as the least mean squared method, could be used to fit this curve. $n_{ij}$ will be close to zero so long as the encoder counters are set to zero at the calibration positions and the relationship between pulse count and length is truly linear. Otherwise, a spline or nonlinear curve fit might be more appropriate for defining the relationship between cable length and pulse count.

The process defined above for finding a linear relationship between encoder counts and cable length could be adapted to include more (or less) calibration positions as described for the calibration process. The user simply moves the point on the tool 160 where the cables 11, 12, 13 and 14 are attached to a specified calibration point. So long as the lengths of all the cables 11, 12, 13 and 14 are known at this point and the encoder counts are recorded at this position, then this data can be used to find a curve fit. The more calibration points the more accurate the curve fit will be.

It is also possible to use cable lengths as determined from alternative tool tracking mechanisms, such as infrared, electromagnetic, gyro or acceleration sensors. These sensors may or may not be fast enough to record tool positions at haptic compatible rates. If such a tracking mechanism is considered accurate, but provides too slow of an update for haptics, the tracking mechanisms might be used to continuously calibrate a tracking system based on the encoders 126 of the tool translation effecter devices 120, 130, 140, 150. The alternative tool tracking mechanisms would yield tool positions, which in turn can be used to determine cable lengths. These lengths can be associated with encoder counter values. A sample of such data can be used to fit a curve, such as that defined by equations 12, to find an updated relationship between cable length and encoder pulses at any given time. This method would therefore not require the user to move to any specific calibration positions. Note that $n_{ij}$ of equation 12 does not have to be zero in this case, if the encoder counters are not set to zero at the calibration positions.

The process to establish in the calculation device 300 a force response that is appropriate at the tool 160 is normally determined according to the software application utilizing the system 10 under discussion. Typically, an application uses the tool 160 position and orientation information to determine if a collision has occurred with virtual objects. The force response can be rendered to simulate a wide range of effects. For example, a force response might simulate a collision of the tool 160 with a rigid or deformable virtual surface, the pull, push, weight or vibration of a virtual object contacting the tool 160, and/or viscous resistance and inertia experienced as a tool 160 moves through virtual fluid. Forces could also be derived from a robot touching real objects where the robot measures the reaction forces upon collision. The only limitation is that the force response determined at the calculation device 300 must be representable as a single vector force in the x, y and z direction at the point(s) where the cables 11, 12, 13, 14 connect with the tool 160. It is this vector force that the user will feel at the tool 160. This vector force can be updated at a rate that is appropriate for the application.

The process for determining tension values in each cable 11, 12, 13, and 14 that will deliver a force vector response to the tool 160 as determined by the calculation device 300 will now be discussed. The force control part 340 calculates tension using the following equation.

$$J = (A\tau - f) + \alpha[\tau]^2$$

for $$A\mathbb{1}y^*$$

$$\min[JJ]^2 \quad A\mathbb{1}y^* \Rightarrow 0 \quad \text{(Eq. 13)}$$

In equation 13, τ is the tension where $\tau = [\tau_1, \tau_2, \tau_3, \tau_4]$ in the cables 11, 12, 13 and 14, α is a coefficient that displays stability of force, J is the target function. Consider $w_i$ (i=11, 12,13,14) ($R^{3\times 1}$) a set of unit force vectors (in 3D) that are displayed along the direction of tension for each cable 11, 12, 13 and 14. $A = \{w_{11}, w_{12}, w_{13}, w_{14}\}$ ($R^{3\times 4}$) is a force matrix filled with the unit vector forces. $f = (f_x, f_y, f_z)$ is the force vector that is to be displayed at the tool 160. The force control 340 calculates positive tension values, which minimizes the target function, J (in other words, J should end up close to zero). A good value to use for α is 0.1, but the teachings herein are not limited to the use of this value. A variety of standard mathematical methods can be used to minimize the target function J and thus determine τ.

The process to control tension in each cable 11, 12, 13, and 14 is accomplished by driving each motor 124, 134, 144 and 154 based on tension values determined in the calculation device 300. The force control part 340 of the control device 300 regulates motor torque by controlling the current sent to the motors 124. Each motor 124 applies torque to the attached spool 126. The torque that accomplishes the appropriate tension in each cable 11 is dependent on the radius of the spool 126, which is accounted for by the force control part 340 of the control device 300.

A wide variety of structures can be used to control the process that relays visual and audible information to the display device 400 from the calculation device 300. Typically, the location and orientation of the tool 160 and virtual or real objects that the tool 160 may be interacting with are displayed graphically. This allows the user to see how he or she is effecting a virtual environment or a robot as the user moves the tool 160. This information is displayed according to the software application utilizing the system 10 under discussion and could constitute a vast range of possible formats. Audio output can also be utilized to display information resulting from tool 160 interaction with virtual objects or real objects encountered through a robot.

There are a variety of configurations that the system 10 can employ that rely on the same concepts outlined above. According to one embodiment of the invention, The system 10 includes a tool shaft 180 that passes through a port 172, and is coupled at one end to the tool or attachment point 160. The cables 11, 12, 13 and 14 are attached to the point 160, which is coupled to the tool shaft 180, which in turn passes through the port 172 of interface device 20, as shown in FIG. 8. While the system 10 applies translation forces in the x, y and z direction through cable 11 tensions to the point 160, or a set of points 160 in close proximity, on the tool shaft 180, the user will feel an insertion force (along with pitch and yaw). In FIG. 8, the insertion force is along the direction of the tool shaft 180 as confined by the port 172. Pitch and yaw are felt at the tool shaft handle with the pivot point at the port 172. Such a configuration is ideal to apply three degrees of freedom force feedback to minimally invasive instruments used when simulating a surgical procedure.

More degrees of force feedback, such as rotation around the tool shaft 180 and grip force at a handle of the tool shaft, can be added through additional motors independent of the cable system. For example, a motor in the tool shaft 180, or attached to the port 172, allows twisting force feedback, and a motor in the handle of the tool shaft 180 adds a squeezing grip force. Such uses of motors to apply simple force feedback over 1 degree of freedom may be used to augment the system 10.

It is common when working through a port 172 to define forces in terms of moment around the port rather than vector forces as applied to the end of the tool attachment point 160. In this case, equation 15 should be adjusted to accommodate moment about the port 172 which can be defined as $M_x$ and $M_y$, and an insertion force $f_I$ which is a vector force in the direction of the shaft of the tool 180.

$$J = (TA\tau - M) + \alpha[\tau]^2 \quad \text{(Eq. 14)}$$

for $$\min[J]^2 \Rightarrow 0$$

-continued and $$T = \begin{bmatrix} 0 & L_z & L_y \\ L_z & 0 & L_x \\ v_x & v_y & v_z \end{bmatrix}$$

In equation 14, consider the port 172 to be located at coordinate $(N_x, N_y, N_z)$ and $L_x=x-N_x$, $L_y=y-N_y$, and $L_z=z-N_z$ where x, y and z can be found using equations 5, 6 and 7. $v=\{v_x, v_y, v_z\}$ is a unit vector that points from the port 172 axis origin (or the port pivot point) toward the point on the tool 160 where the cables 11, 12, 13, 14 are connected. $M=\{M_x, M_y, f_I\}$ are the moment and insertion force values prescribed by the user.

Figure 10:
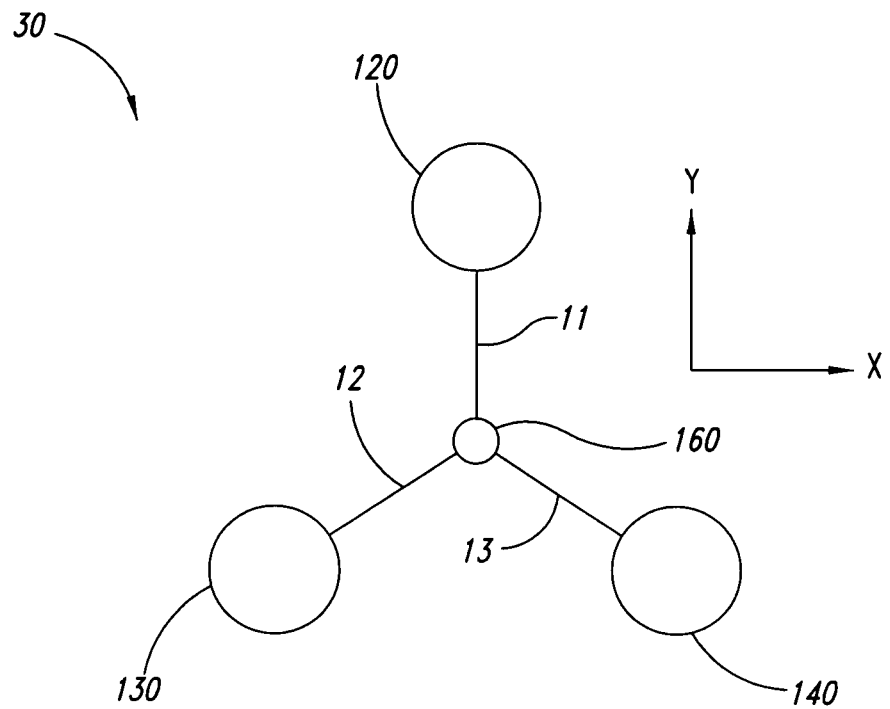
FIG. 10 shows a generalized schematic for rendering force and tracking a tool over two dimensions.

Embodiments of the invention are not limited to three degrees of force feedback freedom. In general, n degrees of force feedback can be accomplished with n+1 cables or feedback devices. FIG. 10 shows the schematic of a simple two-degree of freedom force feedback system 30, according to another embodiment of the invention. The system 30 requires three cables 11, 12, 13 and three tool translation effecter devices 120, 130 and 140. Equations 1, 2 and 3 define the length of the three cables 11, 12 and 13. Assume that tool translation effecter device 120 lies at coordinate (0, b, 0), tool translation effecter device 130 lies at coordinate (−a, −b, 0) and tool translation effecter device 140 lies at coordinate (a, −b, 0). Equations 1, 2 and 3 can be combined to isolate the x and y position values of the tool 160.

$$x = \frac{l_{12}^2 - l_{13}^2}{4a} \quad \text{(Eq. 17)}$$

$$y = \frac{l_{12}^2 + l_{13}^2}{8b} - \frac{l_{11}^2 + a^2}{4b} \quad \text{(Eq. 18)}$$

Equation 13 can be used, with two dimensional coefficient representations, to find two degrees of freedom force feedback in the x and y direction for the configuration shown in FIG. 10. τ is the tension where $\tau=[\tau_{11}, \tau_{12}, \tau_{13}]$ in the cables 11, 12 and 13. Consider $w_i (i=11,12,13)$ ($R^{\epsilon 2 \times 1}$) a set of unit force vectors (in 2D) that are displayed along the direction of tension in each cable 11, 12 and 13 in the x-y plane. $A=\{w_{11}, w_{12}, w_{13}\}$ ($R^{\epsilon 2 \times 3}$) is a force matrix filled with the unit vector forces that correspond to the cables 11, 12 and 13. $f=(f_x, f_y)$ is the 2D force vector that is to be displayed at the tool 160. It should be noted that a force along the z axis will be present if the tool 160 is moved outside of the x-y plane. This force will always pull the tool 160 back toward the x-y plane.

Figure 11:
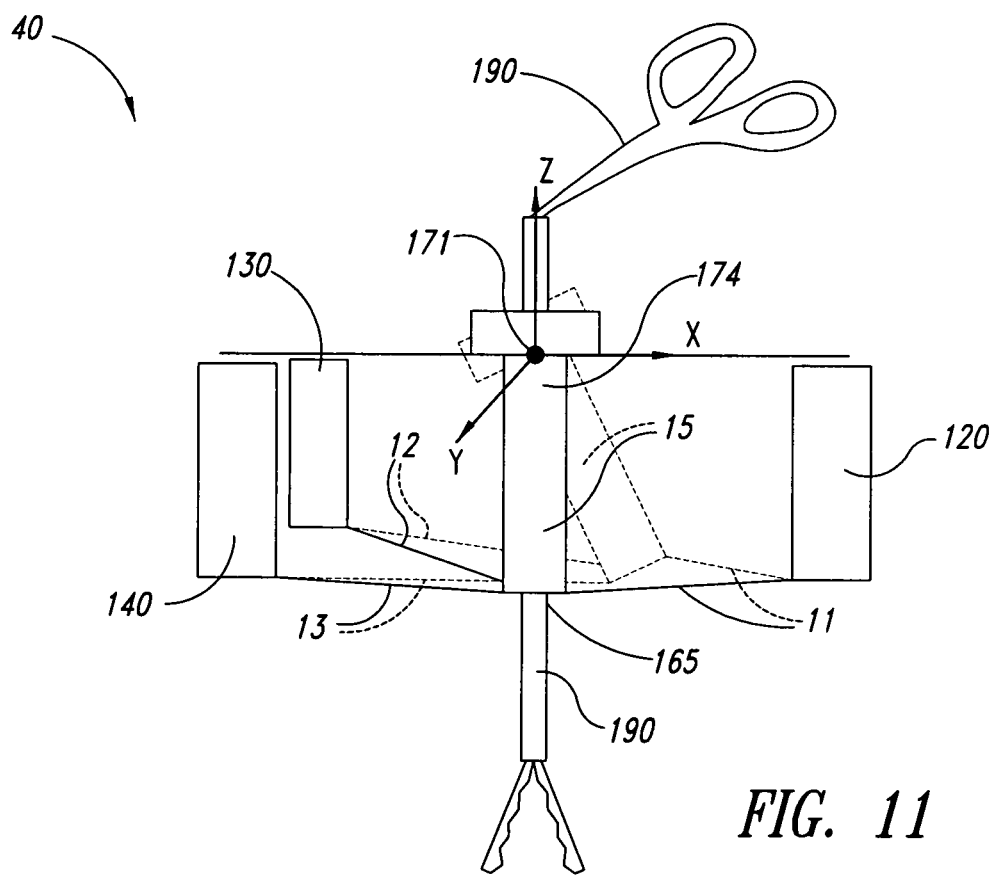
FIG. 11 shows a configuration of the invention that will allow forces to be applied and controlled on a port, or trocar, over two dimensions in a system that might be used for minimally invasive surgery simulation. The system also allows for tracking the position of the point on the port where the cables connect.

FIG. 11 shows an interface device 40, according to another embodiment of the invention. The port 174 is elongated, with an upper end fixed to a pivot point 171, while the point defined in other embodiments as the tool or attachment point 160 is defined in this embodiment as the lower end 165 of the port 174, which is free to move, within the constraints imposed by the device 40. In this configuration, the cables are attached to the lower end 165 of the port 174 rather than the tool 160. The port 174 rotates freely around the port axis origin 171 (or port pivot point) while the tool 190 itself slides freely through the port 174.

When finding the cable tensions that will result in moment about the port 174, which can be defined as $M_x$ and $M_y$, a reduced version of equation 14 can be used. This is because insertion of the tool 190 is not being constrained, so the insertion force is essentially zero. T and M of equation 14 are simply redefined to reflect the two degrees of force feedback problem, as shown below:

$$T = \begin{bmatrix} 0 & L_z & L_y \\ L_z & 0 & L_x \end{bmatrix} \text{ and } M = \{M_x, M_y\}$$

In equation 14, τ is the tension where τ=[τ$_1$,τ$_2$,τ$_3$] in the cables 11, 12 and 13, respectively. Consider w$_i$(i=11,12,13) ($R^{\epsilon 3 \times 1}$) a set of unit force vectors (in 3D) that are displayed along the direction of tension in each cable 11, 12 and 13. A={w$_{11}$,w$_{12}$,w$_{13}$}($R^{\epsilon 3 \times 3}$) is a force matrix filled with the unit vector forces that correspond to the cables 11, 12 and 13.

It may be seen that when the port 174 is rotated on the pivot point 171, the cable connection point 165 of the port 174 moves out of the x-y plane, as shown in dotted lines in FIG. 11. Because f$_z$ does exist when the point 165 is moved out of the x-y plane, it is not straight forward to convert from moments about a port 174 to cable tensions using equation 16. By accounting for the forces that result in the z direction as the cable connection point 165 on the port 174 moves out of the x-y plane when the port 174 is rotated, accurate moments (M={M$_x$, M$_y$}), can be achieved.

While the x, y and z position on the port 174, where the cables 11, 12, 13 attach, can be solved using only equations 1, 2 and 3, it is also convenient to consider the constant length of the port shaft 15 as l$_{14}$. Under this assumption, equations 5, 6 and 7 can be used to determine position. This is only one example of how to determine position for the configuration of FIG. 11. Methods similar to those discussed earlier also apply.

Rotational feedback and gripping force feedback may also be provided for the tool 190 of FIG. 10, as has been described in more detail with reference to the tool shaft 180 of FIG. 8.

Although not shown in any figure, a set of cables may be applied to multiple points on a tool so that different vector forces can be rendered at each point. A single calculation device can be used to control all the cable sets, or different calculation devices, for example on separate circuit boards, may be used. The effect of applying separate force vectors to different points on a single tool yields the effect of rotational forces as felt by the user, or may serve to control the movement of a jointed tool. Multiple sets of cables can also be used to apply force vectors to multiple tools that exist in the same workspace.

Although specific embodiments of and examples for the haptic system and method are described herein for illustrative purposes, various equivalent modifications can be made without departing from the spirit and scope of the invention, as will be recognized by those skilled in the relevant art. The teachings provided herein of the invention can be applied to other haptic systems, not necessarily the exemplary haptic system 10 generally described above.

The various embodiments described above can be combined to provide further embodiments. All of the above U.S. patents, patent applications and publications referred to in this specification are incorporated by reference. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all haptic systems that operate in accordance with the claims. Accordingly, the invention is not limited by the disclosure, but instead its scope is to be determined entirely by the following claims.

All of the above U.S. patents, U.S. patent application publications, U.S. patent applications, foreign patents, foreign patent applications and non-patent publications referred to in this specification and/or listed in the Application Data Sheet, including but not limited to U.S. Pat. No. 5,305,429; Seahak Kim, Masahiro Ishii, Yasuharu Koike, Makoto Sato, "Development of Tension Based Haptic Interface with 7 DOF:SPIDAR-G," ICAT2000, 25-27, Oct., 2000, National Taiwan University, Taiwan; Seahak Kim, Masahiro Ishii, Yasuharu Koike, Makato Sato, "Design of a Tension Based Haptic Interface with 6 DOF," 4th World Multiconference on Systemics, Cybernetics and Informatics (SCI2000) and the 6th International Conference on Information Systems Analysis and Synthesis (ISAS2000), Orlando, USA, in Jul. 23-26, 2000; Seahak Kim, Masahiro Ishii, Yasuharu Koike, Makoto Sato, "Development of SPIDAR-G and Possibility of its Application to Virtual Reality," VRST2000, 22-25, Oct., 2000, Seoul, Korea; Seahak Kim, Masahiro Ishii, Yasuharu Koike, Makoto Sato, "Design of tension based haptic interface: SPIDAR-G," IMECE2000 (joint with ASME2000), 5-10, Nov., 2000, Orlando, USA; Seahak Kim, Masahiro Ishii, Yasuharu Koike, Makoto Sato, "Cutting edge Haptic interface device: SPIDAR-G," Proceedings of the 32nd ISR (International Symposium on Robotics), 19-21, Apr., 2001, Seoul, Korea; Seahak Kim, Shoichi Hasegawa, Yasuharu Koike, Makoto Sato, "Tension Based 7 DOFs Force Feedback Device: SPIDAR-G" by the IEEE Computer Society Press in the proceedings of the IEEE Virtual Reality Conference 2002, 24-28 Mar. 2002 in Orlando, Florida; Seahak Kim, Shouichi Hasegawa, Yasuharu Koike, Makoto Sato, "Tension based 7 DOF Force Feedback Device," Trans. On ICASE, Vol. 4, No. 1, pp. 8-16, 2002; Seahak Kim, Jeffrey J. Berkley, and Makoto Sato, "A Novel Seven Degree of Freedom Haptic Device for Engineering Design," Journal of virtual reality, Springer UK (accepted), are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A haptic interface device to provide haptic interaction to a user manipulating a tool, the haptic interface device comprising:
    an attachment point;
    a plurality of cables coupled to the attachment point, the plurality of cables comprising a first, a second, a third, and a fourth length of cable extending from the attachment point;
    a first tool translation effecter device having a first cable guide, a second tool translation effecter device having a second cable guide, a third tool translation effecter device having a third cable guide, and a fourth tool translation effecter device having a fourth cable guide, the first, the second, the third and the fourth cable guides positioned, relative to each other, such that each of the first, the second, the third, and the fourth cable guides occupies a vertex of a tetrahedron, each tool translation effecter device having coupled thereto, a respective one of the first, the second, the third, and the fourth lengths of cable such that, as the attachment point moves, each of the first, the second, the third, and the fourth lengths of cables is retracted or paid out accordingly by the respective tool translation effecter device, each tool translation effecter device including controlling means for selectively varying an active tension on the respective length of cable;

metering means for metering each of the first, the second, the third, and the fourth length of cables as they are retracted and paid out; and establishing means for establishing a respective distance between each of the first, the second, the third, and the fourth cable guides and the attachment point, the establishing means including a memory configured to receive and store, prior to a complete shutdown of the haptic interface device, the respective distances between each of the first, the second, the third, and the fourth tool translation effecter devices and the attachment point, and to provide the stored distances during a startup procedure.

2. The haptic interface device of claim 1 wherein:

the controlling means of each of the first, the second, the third, and the fourth tool translation effecter devices includes a spool and a motor coupled to rotatably drive the spool, the motor and spool selectively operable to wind and unwind the respective length of cable; and the metering means includes:

counting means for counting fractions of rotations of the spool of each of the first, the second, the third, and the fourth tool translation effecter devices.

3. The haptic interface device of claim 1 wherein the establishing means includes a controller configured to direct the first tool translation effecter device to retract, during an initialization procedure, the first length of cable until the attachment point is at a selected position relative to the first tool translation effecter device.

4. The haptic interface device of claim 1 wherein the controlling means of each of the first, the second, the third, and the fourth tool translation effecter devices includes a rotatably driven spool, selectively operable to wind and unwind the respective length of cable, wherein the establishing means includes at least four brakes, each respective brake coupled to respective ones of the first, the second, the third, and the fourth tool translation effecter devices, and each respective brake configured to prevent rotation of the respective spool of the respective translation effecter device coupled thereto when actuated.

5. The haptic interface device of claim 1 wherein the establishing means includes a sensor configured to sense, independent of the first tool translation effecter device, a position of the attachment point relative to the first tool translation effecter device and wherein the establishing means includes means for calibrating the first, the second, the third and the fourth translation effecter devices based at least on the sensed position of the attachment point.

6. The haptic interface device of claim 1 wherein the establishing means includes means for reestablishing the respective distances from time to time during a period of time in which the first, the second, the third and the fourth tool translation effecter devices are continuously powered and includes means for calibrating the first, the second, the third and the fourth translation effecter devices during the period of time based at least on the respective reestablished distances.

7. The haptic interface device of claim 1, further comprising:

a sensor array at the attachment point configured to provide signals corresponding to an orientation of the attachment point.

8. The haptic interface device of claim 7 wherein the sensor array is configured to provide signals corresponding to roll, pitch, and yaw of the attachment point.

9. The haptic interface device of claim 1 wherein the establishing means comprises a calibration point at which the attachment point can be positioned, and from which the respective distances between each of the first, the second, the third, and the fourth cable guides and the attachment point are known.

10. The haptic interface device of claim 1 wherein controlling means of each of the first, the second, the third, and the fourth tool translation effecter devices includes a rotatably driven spool, selectively operable to wind and unwind the second end of the respective cable;

wherein metering means includes at least four encoders, each respective encoder arranged to provide signals corresponding to rotation of a respective spool of a respective translation effecter device; and wherein establishing means includes at least four brakes, each respective brake coupled to respective ones of the first, the second, the third, and the fourth tool translation effecter devices, and each respective brake configured to lock in position a respective encoder when actuated.

11. A haptic interface device to provide haptic interaction to a user manipulating a tool, the haptic interface device comprising:

an attachment point configured to receive the tool and to be moved at least within a workspace;

a plurality of not more than four lengths of cables and a plurality of not more than four cable guides, each length of cable coupled to the attachment point and extending to a respective cable guide of the plurality of cable guides;

a plurality of tool translation effecter devices, each having a spool with an end of a respective one of the plurality of cables coupled thereto such that, as the attachment point moves relative to that tool translation effecter device, the cable coupled thereto is retracted or paid out accordingly, each tool translation effecter device configured to selectively vary an active tension on the cable coupled thereto; and a first, a second, a third, and a fourth brake, each respective brake coupled to a respective tool translation effecter device of the first, the second, the third, and the fourth tool translation effecter devices and configured to prevent rotation, prior to a power down of the haptic interface device and while the haptic interface device is powered down, of the respective spool of the respective tool translation effecter device having the respective brake coupled thereto in response to a controlled power down signal.

12. The haptic interface device of claim 11 wherein the plurality of tool translation effecter devices includes at least a first, a second, a third, and a fourth tool translation effecter device, each of the first, the second, the third, and the fourth tool translation effecter devices having a respective cable guide of the plurality of cable guides, and where the respective cable guides are positioned relative to each other such that each respective cable guide occupies a vertex of a tetrahedron.

13. The haptic interface device of claim 11, further comprising:
    establishing means for establishing, during an initialization procedure, a distance between each of the tool translation effecter devices and the attachment point.

14. The haptic interface device of claim 13 wherein the establishing means includes a sensor array is configured to provide signals corresponding to each of a roll, a pitch, and a yaw of the tool.

15. The haptic interface device of claim 11, further comprising a sensor array associated with the attachment point and configured to provide signals corresponding to at least one of roll, pitch, and yaw of the tool.

16. The haptic interface device of claim 11 wherein each respective tool translation effecter device of the plurality of tool translation effecter devices includes a respective encoder configured to provide a signal corresponding to rotation of the respective spool of the respective tool translation effecter device, and wherein each respective brake selectively locks in position the respective encoder of the respective tool translation effecter device having the respective brake coupled thereto when actuated.

17. A haptic device for operation by a user, comprising:
    a user interface tool configured to be manipulated by the user and moved within a volume of space;
    a first, a second, a third, and a fourth tool translation effecter device, each tool translation effecter device including a respective cable guide component coupled to a support structure in positions such that the respective cable guide components define between them a tetrahedron within the volume of space, each of the tool translation effecter devices further including a respective spool, a respective motor, and a respective encoder configured to provide a signal corresponding to rotation of the respective spool; and
    a plurality of cables coupled to the user interface tool and comprising at least a first segment of cable, a second segment of cable, a third segment of cable and a fourth segment of cable extending from the user interface tool, and wherein an end of each of the first, the second, the third, and the fourth segments of cable are wound and unwound on the spool of a respective one of the tool translation effecter devices, each of the motors operable to drive the respective spool; and
    a first, a second, a third, and a fourth brake, each brake coupled to a respective tool translation effecter device of the first, the second, the third, and the fourth tool translation effecter devices and configured to prevent rotation, prior to a power down of the haptic interface device and while the haptic interface device is powered down, of the respective spool of the respective tool translation effecter device having the brake coupled thereto in response to a controlled power down signal.

18. The haptic device of claim 17, comprising a sensor array configured to detect roll, pitch, and yaw of the user interface tool.

19. The haptic device of claim 18, further comprising a processor system coupled to receive information from the sensor array and coupled to receive the signals from the respective encoders, the processor system configured to determine movement and orientation of the tool therefrom.

20. The haptic device of claim 17, comprising a processor system that receives the signals from the respective encoders, the processor system configured to determine movement of the user interface tool therefrom.

21. The haptic device of claim 20 wherein the processor system is configured to compensate for changes in effective diameter of the spools of the first, the second, the third, and the fourth tool translation effecter devices due to the respective cable being wound and unwound from the respective spool.

22. The haptic device of claim 20 wherein the processor system is configured to establish an initial position of the tool by retracting, in turn, each of the first, the second, the third, and the fourth segments of cable to a known length position.

23. The haptic device of claim 20 wherein the processor system is configured to maintain a virtual environment within which the user interface tool is operated, and to apply the actual force vector as feedback from the virtual environment to the user interface tool.

24. The haptic device of claim 17, further comprising:
    a remote tool; and
    a processor system in communication with the remote tool and configured to control operation of the remote tool in accordance with the movement and orientation of the user interface tool.

25. The haptic device of claim 24 wherein the processor system is configured to apply an actual force vector as feedback from the remote tool to the user interface tool.

26. The haptic device of claim 17 wherein the device comprises no more than four cables.

27. The haptic interface device of claim 17 wherein each respective brake selectively locks in position the respective encoder of the respective tool translation effecter device having the respective brake coupled thereto when actuated.

28. A haptic device for operation by a user, comprising:
    a support structure;
    a port coupled to the support structure;
    a user interface tool configured to be manipulated by the user and moved within a volume of space, the user interface tool includes a tool shaft having a first and a second end, the tool shaft passing through the port such that the tool shaft pivots at the port and manipulation of the second end of the tool shaft is reflected in movement of the first end of the tool shaft;
    a first, a second, a third, and a fourth tool translation effecter device, each coupled to the support structure in positions such that the first, the second, the third, and the fourth tool translation effecter devices define between them a tetrahedron within the volume of space, each of the tool translation effecter devices including a respective spool and a respective encoder configured to provide a signal corresponding to rotation of the respective spool; and
    a first, a second, a third, and a fourth length of cable, each of the first, the second, the third, and the fourth length of cable being coupled to the first end of the tool shaft and each of the first, the second, the third, and the fourth lengths of cable being wound and unwound on the spool of a respective one of the tool translation effecter devices.

29. The haptic device of claim 28, further comprising:
    a first sensor located at the port and coupled to the tool shaft, and configured to detect rotation of the user interface tool around an axis.

30. The haptic device of claim 28, further comprising:
    a first sensor configured to detect rotation of the user interface tool around an axis, and a second sensor coupled to the second end of the tool shaft and configured to detect gripping force exerted by the user.

31. The haptic device of claim 28 wherein the second end of the tool shaft is configured to provide for the user a simulation of a selected tool.

32. The haptic device of claim 31 wherein the selected tool is formed as one of a stylus, a pen, a pliers, a wrench, a forceps, a scalpel, an endoscope, or an arthroscope.

33. The haptic device of claim 28, further comprising:
a feedback device coupled to the tool shaft and configured to selectively apply rotational force to the tool shaft.

34. The haptic device of claim 33 wherein the feedback device is located at the port.

35. The haptic device of claim 28, further comprising:
a feedback device coupled to the second end of the tool shaft and configured to selectively resist gripping force exerted by the user.

36. A method, comprising:
applying a selectively variable active tension to each of a plurality of cables having respective first and second ends, each of the plurality of cables coupled at its respective first end to a tool, and at its respective second end to a respective anchor point;
measuring a change of cable length between the tool and each respective anchor point;
establishing an initial length of cable between the tool and each of the anchor points;
locking, during a shutdown procedure, each of the plurality of cables at the respective anchor point;
storing, after the locking and before completing the shutdown procedure, a value indicative of a known length of each of the cables in a memory; and
recovering the value indicative of the known length of each of the cables from the memory during a startup procedure.

37. The method of claim 36 wherein establishing an initial length of cable comprises moving the tool in turn to each vertex of a tetrahedron such that the length of cable between the tool and the respective the respective vertex is effectively zero, wherein a respective cable guide is positioned at each of the vertices of the tetrahedron.

38. The method of claim 36 wherein establishing an initial length of cable comprises:
tracking a position of the tool independent of the measuring; and
correlating the position of the tool with known positions of the anchor points.

39. A method of operating a cable based haptic interface device having four segments of cable and a specified calibration point, comprising:
releasing four segments of cable in response to the cable based haptic interface device being powered on, wherein prior to the cable based haptic interface device being powered on the four segments of cable are locked;
during a calibration of a cable based haptic interface device, positioning a tool having the four segments of cable coupled thereto at a specified single calibration point from which respective reference lengths of each of the four segments of cable is known, each segment of cable coupled to the tool and having a respective length extending from the tool to a respective vertex of a tetrahedron such that, as the tool is moved closer to any respective vertex of the tetrahedron, the respective length of the segment of cable extending from the tool to the respective vertex is drawn in, thereby decreasing the respective length of the respective segment of cable, and as the tool is moved away from any respective vertex of the tetrahedron, the respective length of the segment of cable extending from the tool to the respective vertex is fed out, thereby increasing the respective length of the respective segment of cable;
establishing the respective length of each of the four segments of cable based at least on the tool being positioned at the calibration point and on the respective reference lengths of each of the four segments of cable;
selectively applying active tension to each of the four segments of cable;
tracking changes in length of each of the four segments of cable; and
deriving a change of position of the tool on the basis of tracked changes in length of each of the four segments of cable.

40. The method of claim 39, comprising measuring rotation of the tool about one or more of three mutually perpendicular axes.

41. The method of claim 39, further comprising selecting a value of active tension applied to each of the four cable segments on the basis of the selected force vector that corresponds to the actual response feedback force vector to be applied to the tool.

42. The method of claim 39 wherein positioning a tool having four cables coupled thereto at a specified single calibration point from which respective reference lengths of each of the four cables is known includes manually positioning the tool at the specified single calibration point.

43. A method of operating a haptic device having a tool coupled to a first end of a first cable, comprising:
as a tool is moved in a first direction, winding a first cable having a first end coupled to the tool onto a spool;
as the tool is moved in a second direction which is opposite the first direction, unwinding the first cable from the spool;
locking, during a shutdown procedure, the first cable at the spool;
storing a value indicative of a known length of the first cable in a memory; and
recovering the value indicative of the known length of the first from the memory during a startup procedure.

44. The method of claim 43 wherein the first cable is one of a plurality of cables having respective first and second ends, the first ends coupled to the tool and the respective second ends coupled to respective spools, and further comprising:
for each respective cable of the plurality of cables,
winding the respective cable onto a respective spool as the tool is moved in a respective first direction,
unwinding the respective cable from the respective spool as the tool is moved in a respective second direction which is opposite the respective first direction,
tracking a respective paid-out cable amount for each respective cable by counting fractional rotations of each of the respective spools, and
limiting tracking errors introduced by changes in an effective diameter of the respective spool of the respective cable as the effective diameter changes in response to the respective cable being wound and unwound therefrom.

45. The method of claim 43 wherein the first cable is one of three cables, each cable having a respective first end coupled to the tool and providing a plane in which the tool has freedom to move, the plane defined by three cable guides, wherein each respective cable extends from the tool and to a respective one of the three cable guides.

46. The method of claim 43 wherein the first cable is one of four cables, each cable having a respective first ends coupled to the tool and providing a volume of space in which the tool has freedom to move defined four cable guides positioned at respective vertices of a tetrahedron, wherein each respective cable extends from the tool and to a respective one of the four cable guides.

47. A method of operating a cable based haptic device having a plurality of cables and a plurality of cable guides, comprising:

for each segment of cable coupled to a tool and extending between the tool and a respective cable guide of a plurality of cable guides and further extending therefrom to a respective anchor point of a plurality of anchor points, applying a selectively variable active tension to the respective segment of cable;

measuring a change of length of the segment of cable between the tool and each respective cable guide of the plurality of cable guides;

establishing an initial length of cable between the tool and each cable guide of the plurality of cable guides;

locking, during a shutdown procedure, each of the plurality of segments of cable at the respective anchor point;

storing, after the locking and before completing the shutdown procedure, a value indicative of a known length of each of the segments of cable in a memory; and recovering the value indicative of the known length of each of the segments of cable from the memory during a startup procedure.

48. The method of claim 47 wherein establishing an initial length of cable comprises moving the tool in turn to each vertex of a tetrahedron such that the length of cable between the tool and the respective the respective vertex is effectively zero, wherein a respective cable guide is positioned at each of the vertices of the tetrahedron.

49. The method of claim 47 wherein establishing an initial length of cable comprises:

tracking a position of the tool independent of the measuring; and correlating the position of the tool with known positions of the anchor points.

* * * * *